US010726954B2

(12) United States Patent
Su et al.

(10) Patent No.: US 10,726,954 B2
(45) Date of Patent: Jul. 28, 2020

(54) PREDICTIVE MODELING OF RESPIRATORY DISEASE RISK AND EVENTS

(71) Applicant: Reciprocal Labs Corporation, Madison, WI (US)

(72) Inventors: Guangquan Su, Alameda, CA (US); Meredith Ann Barrett, Redwood City, CA (US); Olivier Humblet, Palo Alto, CA (US); Chris Hogg, San Francisco, CA (US); John David Van Sickle, Oregon, WI (US); Kelly Anne Henderson, San Francisco, CA (US); Gregory F. Tracy, Madison, WI (US)

(73) Assignee: RECIPROCAL LABS CORPORATION, Madison, WI (US)

( * ) Notice: Subject to any disclaimer, the term of this patent is extended or adjusted under 35 U.S.C. 154(b) by 838 days.

(21) Appl. No.: 15/136,667

(22) Filed: Apr. 22, 2016

(65) Prior Publication Data
US 2016/0314256 A1 Oct. 27, 2016

Related U.S. Application Data

(60) Provisional application No. 62/151,392, filed on Apr. 22, 2015.

(51) Int. Cl.
*G16H 50/20* (2018.01)
*G06F 19/00* (2018.01)
*G06N 20/00* (2019.01)

(52) U.S. Cl.
CPC ......... *G16H 50/20* (2018.01); *G06F 19/3462* (2013.01); *G06N 20/00* (2019.01); *Y02A 90/24* (2018.01); *Y02A 90/26* (2018.01)

(58) Field of Classification Search
None
See application file for complete search history.

(56) References Cited

U.S. PATENT DOCUMENTS

| 6,693,546 B2 * | 2/2004 | Skardon | G06F 19/3418 340/627 |
| 9,747,419 B2 * | 8/2017 | Zhang | G06Q 40/12 |

(Continued)

OTHER PUBLICATIONS

Aldrin, M. et al., "Generalised Additive Modelling of Air Pollution, Traffic Volume and Meteorology," Atmos Environ, 2005, pp. 2145-2155, vol. 39.

(Continued)

*Primary Examiner* — Tracy C. Chan
(74) *Attorney, Agent, or Firm* — Fenwick & West LLP

(57) ABSTRACT

An application server predicts respiratory disease risk, rescue medication usage, exacerbation, and healthcare utilization using trained predictive models. The application server includes model modules and submodel modules, which communicate with a database server, data sources, and client devices. The submodel modules train submodels by determining submodel coefficients based on training data from the database server. The submodel modules further determine statistical analysis data and estimates for medication usage events, healthcare utilization, and other related events. The model modules combine submodels to predict respiratory disease risk, exacerbation, rescue medication usage, healthcare utilization, and other related information. Model outputs are provided to users, including patients, providers, healthcare companies, electronic health record systems, real estate companies and other interested parties.

20 Claims, 13 Drawing Sheets

(56) References Cited

U.S. PATENT DOCUMENTS

| | | | |
|---|---|---|---|
| 2002/0186137 A1 | 12/2002 | Skardon | |
| 2009/0313605 A1* | 12/2009 | Ostrand | G06F 11/008 717/124 |
| 2013/0197942 A1* | 8/2013 | Chiu | G06Q 50/22 705/3 |
| 2013/0317379 A1* | 11/2013 | Brimer | A61B 5/087 600/538 |
| 2016/0283686 A1* | 9/2016 | Hu | G06N 5/04 |

OTHER PUBLICATIONS

Beckerman, B.S. et al., "A Hybrid Approach to Estimating National Scale Spatiotemporal Variability of PM2.5 in the Contiguous United States," Environ Sci Technol, 2013, pp. 7233-7241, vol. 47.

Chan, A.H. et al., "Using Electronic Monitoring Devices to Measure Inhaler Adherence: A Practical Guide for Clinicians," The Journal of Allergy and Clinical Immunology: In Practice, May/Jun. 2015, pp. 335-349, vol. 3, Iss. 3.

Howard, S. et al., "Electronic Monitoring of Adherence to Inhaled Medication in Asthma," Current Respiratory Medicine Reviews, 2014, pp. 50-63, vol. 10.

Jerrett, M. et al., "A Review and Evaluation of Intraurban Air Pollution Exposure Models," J Expo Anal Env Epid, 2005, pp. 185-204, vol. 15.

Patel, M. et al., "Metrics of Salbutamol Use as Predictors of Future Adverse Outcomes in Asthma," Clinical & Experimental Allergy, 2013, pp. 1144-1151, vol. 43.

Patel, M. et al., "Short-Acting 13-Agonist Use as a Marker of Current Asthma Control," J Allergy Clin Immunol Pract, 2013, pp. 370-377, vol. 1, No. 4.

PCT International Search Report and Written Opinion, PCT Application No. PCT/US16/29025, dated Aug. 4, 2016, 14 pages.

Reddel, H.K., "An Official American Thoracic Society/European Respiratory Socity Statement: Asthma Control and Exacerbations: Standardizing Endpoints for Clinical Asthma Trials and Clinical Practice," American Journal of Respiratory and Critical Care Medicine, 2009, pp. 59-99, vol. 180.

Su, J.G. et al., "Integrating Smart-Phone Based Momentary Location Tracking with Fixed Site Air Quality Monitoring for Personal Exposure Assessment," Sci Total Environ, 2015, pp. 506-507, 518-526.

Tsiros, I.X. et al., "Estimating Airborne Pollutant Concentrations in Vegetated Urban Sites Using Statistical Models with Microclimate and Urban Geometry Parameters as Predictor Variables: A Case Study in the City of Athens Greece," J Environ Sci Heal A, 2009, pp. 1496-1502, vol. 44.

Van Sickle, D. et al., "Remote Monitoring of Inhaled Bronchodilator Use and Weekly Feedback about Asthma Management: An Open-Group, Short-Term Pilot Study of the Impact on Asthma Control," PLoS One, Feb. 2013, pp. 1-4, vol. 8, Iss. 2.

* cited by examiner

PREDICTIVE MODELING OF RESPIRATORY DISEASE RISK AND EVENTS

CROSS REFERENCE TO RELATED APPLICATION

This application claims the benefit of U.S. Provisional Patent Application Ser. No. 62/151,392, filed Apr. 22, 2015, the contents of which are incorporated herein by reference.

BACKGROUND

Medicament devices such as inhalers allow patients to manage respiratory symptoms such as constricted airflow. Many respiratory disease patients, such as sufferers of asthma, COPD, and cystic fibrosis, have symptoms that are related to environmental triggers and factors such as air quality, weather, land use, and the like. A patient being aware of which environmental triggers and factors affect their symptoms allows the patient to better manage their symptoms and reduce the chances for needing emergency medical care. However, a particular patient or group of patients may have sensitivities to multiple triggers and factors. Knowing which of dozens, hundreds, or more triggers and factors a patient is sensitive to and monitoring those triggers and factors for use in managing symptoms is a complex task and not a reasonable strategy for many patients and providers.

DETAILED DESCRIPTION

I. System Environment

Figure 1A:
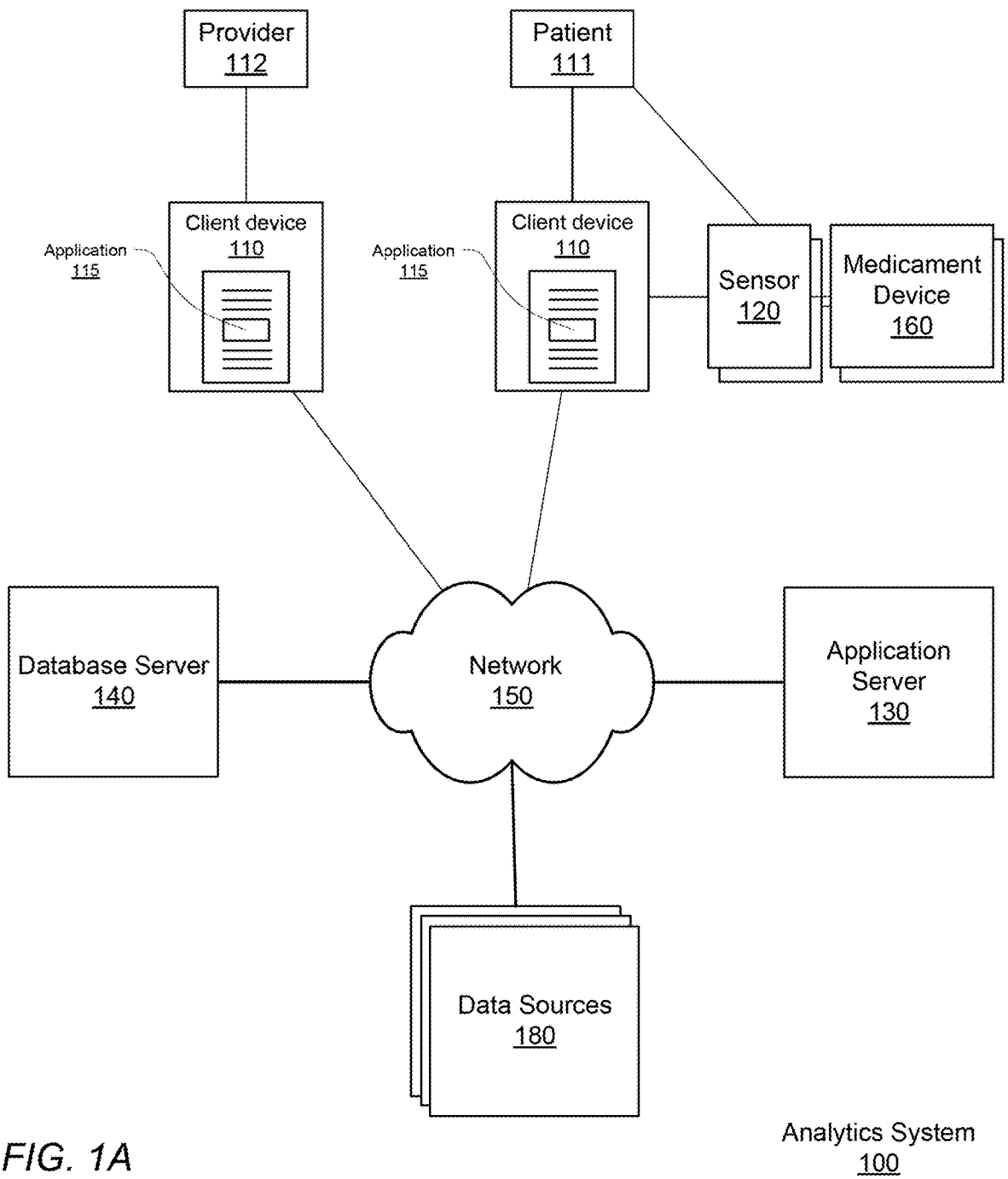
FIG. 1A shows an analytics system for monitoring accurate, real-time medicament device usage, performing analytics on that data, and providing notifications according to the analytics, according to one embodiment.

FIG. 1A shows an analytics system 100 for monitoring accurate, real-time medicament device events, performing analytics on that data, and providing notifications, according to one embodiment.

The analytics system includes client computing devices 110, a medicament device sensor 120, a medicament device 160, an application server 130, database server 140, data sources 180, and a network 150. Although FIG. 1A illustrates only a single instance of most of the components of the analytics system 100, in practice more than one of each component may be present, and additional or fewer components may be used.

I.A. Client Device and Application

The client devices 110, at the behest of their users, interact with the analytics system 100 via the network 150. For purposes of explanation and clarity it is useful to identify at least two different types of users. A patient 111 is a user burdened with respiratory impairment, also referred to herein as respiratory disease, who makes use of the analytics system 100 at least in part to obtain personalized notifications provided by the server 130 and by their health care provider 112. Examples of respiratory diseases include asthma, chronic obstructive pulmonary disease (COPD), and cystic fibrosis, lung cancer, chronic bronchitis, influenza, and pneumonia. Such notifications can be provided in exchange for the user's permission to allow the analytics system 100 to monitor the patient's 111 medicament device 160 usage. As will be explained below, medication events are detected by a sensor 120 associated with the medicament device 160 and the user's client device 100, which in turn reports to the application server 130, which in turn can initiate a process to generate risk notifications which are provided to the user through the client device 110.

Another type of user is a healthcare provider 112 who, again with the patient's 111 express permission, also receives notifications regarding a patient's management, as well as aggregated rescue or controller medication event data and derived statistics based on these events and other associated data. Other types of users are also contemplated, such as parents/guardians of patients 111 who may also wish to receive notifications in the event that their own client devices 110 are distinct from that of their children.

The client device 110 is a computer system, an example physical implementation which is described more completely with respect to FIG. 2, below. The client device 110 is configured to wirelessly communicate with the analytics system 100 via network 150. With network 150 access, the client device 110 transmits to system 100 the user's geographical location and the time of a controller or rescue medication event, as well as information describing the event as received from the associated medicament device sensor 120 (referred to throughout as "sensor 120").

Regarding user location and event times, the client device 110 may determine the geographical location and time of a rescue event through use of information about the cellular or wireless network 150 to which it is connected. For example, the current geographical location of the client device 110 may be determined by directly querying the software stack providing the network 150 connection. Alternatively, the geographical location information may be obtained by pinging an external web service (not shown in FIG. 1A) made accessible via network 150. The time of an event can be provided by the sensor 120 as part of the event data or added to event data by querying an appropriate software routine available as part of the client device's native operating system.

In addition to communicating with the application server 130, client devices 110 connected wirelessly to the analytics system 100 may also exchange information with other connected client devices 110. For example, through a client software application 115, a healthcare provider 112 may receive a risk exacerbation notification describing a recent rescue event about a patient 111, then in response send a recommendation to the patient 111 for post-chronic obstructive pulmonary disease (COPD) exacerbation treatment. Similarly, through application 115 patients 111 may communicate with their health care providers 112 and other patients 111.

Application 115 provides a user interface (herein referred to as a "dashboard") that is displayed on a screen of the client device 110 and allows a user to input commands to control the operation of the application 115. The dashboard is the mechanism by which healthcare providers 112 and patients 111 access the analytics system 100. For example, the dashboard allows patients 111 and providers 112 to interact with each other, receive notifications, exchange messages about treatment, provide and receive additional event and non-event data, and so on. Application 115 may be coded as a web page, series of web pages, or content otherwise coded to render within an internet browser. Application 115 may also be coded as a proprietary application configured to operate on the native operating system of the client device 110. The dashboard is more completely described below in conjunction with FIG. 3.

In addition to providing the dashboard, application 115 may also perform some data processing on rescue and controller medication event data locally using the resources of client device 110 before sending the processed data through the network 150. Event data sent through the network 110 is received by the application server 130 where it is analyzed and processed for storage and retrieval in conjunction with database server 140. The application server 130 may direct retrieval and storage request to the database system 130 as required by the client application 115.

The client device 110 communicates with the sensor 120 using a network adapter and either a wired or wireless communication protocol, an example of which is the Bluetooth Low Energy (BTLE) protocol. BTLE is a short-ranged, low-powered, protocol standard that transmits data wirelessly over radio links in short range wireless networks. After the sensor 120 and client device 110 have been paired with each other using a BTLE passkey, the sensor 120 automatically synchronizes and communicates information relating to medicament device usage with the client device 110. If the sensor 120 has not been paired with a client device 110 prior to a rescue medication event, the information is stored locally until such a pairing occurs. Upon pairing, the sensor 120 communicates any stored event records to the client device 110. In other implementations, other types of wireless connections, e.g., infrared or 802.11.

Although client devices 110 and medicament devices 160 are described above as being separate physical devices (such as smart phones and inhalers, respectively), in the future it is contemplated the medicament devices 160 may include not only sensors 120 integrated into a single housing with the device 160, but also aspects of the client device 110. For example, a medicament device 160 may include an audio-visual interface including a display or other lighting elements as well as speakers for presenting visual audible information. In such an implementation the medicament device 160 itself may present the contents of notifications provided by the server 130 directly, in place of or in addition to presenting them through the client devices 110.

I.B. Medicament Device and Sensor

The medicament device 160 is a medical device used to deliver medication to the lungs of a user experiencing constricted respiratory airflow. Medicament devices (e.g. inhalers) are typically portable and small enough to be carried by hand for ease of accessibility when treating respiratory attacks. In one embodiment, medicine is delivered in aerosol form through a medicament device 160 such as a metered dose inhaler. Metered dose inhalers included a pressured propellant canister of aerosol medicine, a metering valve for delivering a regulated medicine dosage amount, and a plastic holder that holds the pressurized canister and also forms a mouthpiece for delivery of the medicine. In another embodiment, medicine is delivered in dry powder form through a medicament device 160 such as a dry powder inhaler. Dry powder inhalers may have Cartesian ovular shaped bodies that house wheel and gear mechanisms enabling a user to index through a strip of dry powder medication. The bodies of dry powder inhalers also include a manifold and a mouthpiece to deliver dry powder to the user. Examples of controller medications that are dispensed by a controller medicament device 160 include beclomethasone, budesonide, and fluticasone as well as combinations of those medications with a long-acting bronchodilator such as salmeterol or formoterol. Examples of rescue medications that are dispensed by a rescue medicament device 160 include albuterol, salbutamol, levalbuterol, metaproterenol, and terbutaline.

Each patient may be associated with more than one medicament device 160. For example, the patient may have a rescue medicament device 160 that dispenses rescue medication, and a controller medicament device 160 that dispenses controller medication. Similarly, each patient may be associated with more than one sensor 120, each chosen to operate with one of the patient's medicament devices 160.

Generally, a sensor 120 is a physical device that monitors the usage of the medicament dispenser 160. The sensor 120 is either removably attachable to the medicament dispenser without impeding the operation of the medication dispenser, or the sensor 120 is an integrated component that is a native part of the medicament dispenser 160 as made available by its manufacturer.

The sensor 120 includes its own network adapter (not shown) that communicates with the client device 110 either through a wired connection, or more typically through a wireless radio frequency connection. In one embodiment, the network adapter is a Bluetooth Low Energy (BTLE) wireless transmitter, however in other embodiments other types of wireless communication may be used (e.g., infrared, 802.11).

The sensor 120 may also be configured to communicate more directly with the application server 130. For example, if the network adapter of the sensor 120 is configured to communicate via a wireless standard such as 802.11 or LTE, the adapter may exchange data with a wireless access point such as a wireless router, which may in turn communicate with the application server 130 without necessarily involving the client device 110 in every exchange of data. These two methods of communicating are not mutually exclusive, and the sensor 120 may be configured to communicate with both the client device 110 and the application server 130, for example using redundant transmission to ensure event data arrives at the application server 130 or to provide information directly to the client device 110 while the application server 130 is determining what notification to provide in response to an event.

As introduced above, the sensor 120 captures data about usage of the medicament device 160. Specifically, each sensor 120 captures the date and time of either controller or rescue medication event, that is, usages of either the controller or rescue medicament device 160, respectively, by the patient 111. Each sensor 120 transmits the event data in real-time or as soon as a network connection is achieved, automatically without input from the patient 111 or health care provider 112. The medication event information is sent to the application server 130 for use in analysis, generation of notifications, and aggregate analyses of event data across multiple patients.

To accomplish this goal, there are a number of different ways for the sensor 120 to be constructed, and in part the construction will depend upon the construction of the medicament device itself 160. Generally, all sensors 120 will include an onboard processor, persistent memory, and the network adapter mentioned above that together function to record, store, and report medication event information to the client device 110 and/or server 130. Sensors 120 may also include a clock for recording the time and date of events.

Regarding specific sensor 120 constructions, traditional inhalers, such as mechanical dose counters, are not designed with sensors 120 in mind, and thus the sensor 120 may be constructed accordingly. Some implementations in this manner include mechanical, electrical, or optical sensors to detect movement of the device 160, priming of the device, activation of the device, inhalation by the user, etc. In contrast, modern inhalers, such as deflectable membrane dose counters, include electrical circuitry may report event information as an electrical data signal which a sensor 120 is designed to receive and interpret, for example the medicament device 160 itself may report movement, priming, and activation to the sensor 120.

More information regarding hardware and software components for the sensors 120 and medicament devices 160, as well as the interaction between them to record one or both of controller and rescue medication events can be found in U.S. patent application Ser. No. 12/348,424, filed Jan. 1, 2009, and International Application No. PCT/US2014/039014, filed May 21, 2014, both of which are incorporated by reference herein in their entirety.

I.C. Application Server

The application server 130 is a computer or network of computers. Although a simplified example is illustrated in FIG. 2, typically the application server will be a server class system that uses powerful processors, large memory, and faster network components compared to a typical computing system used, for example, as a client device 110. The server typically has large secondary storage, for example, using a RAID (redundant array of independent disks) array and/or by establishing a relationship with an independent content delivery network (CND) contracted to store, exchange and transmit data such as the notifications contemplated above. Additionally, the computing system includes an operating system, for example, a UNIX operating system, LINUX operating system, or a WINDOWS operating system. The operating system manages the hardware and software resources of the application server 130 and also provides various services, for example, process management, input/output of data, management of peripheral devices, and so on. The operating system provides various functions for managing files stored on a device, for example, creating a new file, moving or copying files, transferring files to a remote system, and so on.

The application server 130 includes a software architecture for supporting access and use of the analytics system 100 by many different client devices 110 through network 150, and thus at a high level can be generally characterized as a cloud-based system. The application server 130 generally provides a platform for patients 111 and healthcare providers 112 to report data recorded by the sensors associated with their medicament devices 160 including both rescue medication and controller medication events, collaborate on treatment plans, browse and obtain information relating to their condition and geographic location, and make use of a variety of other functions.

Generally, the application server 130 is designed to handle a wide variety of data. The application server 130 includes logical routines that perform a variety of functions including checking the validity of the incoming data, parsing and formatting the data if necessary, passing the processed data to a database server 140 for storage, and confirming that the database server 140 has been updated.

The application server 130 stores and manages data at least in part on a patient by patient basis. Towards this end, the application server 130 creates a patient profile for each user. The patient profile is a set of data that characterizes a patient 111 of the analytics system 100. The patient profile may include identify information about the patient such as age, gender, current rescue medication, current controller medication, notification preferences, a controller medication adherence plan, and a list of non-patient users authorized to access to the patient profile. The profile may further specify a device identifier, such as a unique media access control (MAC) address identifying the one or more client devices 110 or sensors 120 authorized to submit data (such as controller and rescue medication events) for the patient.

The profile may specify which different types of notifications are provided to themselves and their personal healthcare provider 112, as well as the frequency with which notifications are provided. The patient may also authorize their healthcare provider be given access to their patient profile and rescue event history. If the healthcare provider is provided access to the patient profile of the patient, the healthcare provider may specify controller adherence or rescue medication plans. Medication plans may include a prescribed number of doses per day for controller medications.

The application server 130 also creates profiles for health care providers 112. A health care provider profile may include identifying information about the health care provider, such as the office location, qualifications and certifications, and so on. The health care provider profile also includes information about their patient population. The provider profile may include access to all of the profiles of that provider's patients, as well as derived data from those profiles such as aggregate demographic information, rescue and controller medication event patterns, and so on. This data may be further subdivided according to any type of data stored in the patient profiles, such as by geographic area (e.g., neighborhood, city) over by time period (e.g., weekly, monthly, yearly).

The application server 130 receives rescue medication event information from the client device 110 or the sensor 120, triggering a variety of routines on the application server 130. For example, a risk analysis may be performed on rescue and controller medication use for multiple patients to identify based on spatial/temporal clusters (or outbreaks) of medication use based on historically significant permutations from individual, geographic, clinical, epidemiologic, demographic, or spatial or temporal baselines or predicted or expected values. Other types of analyses include daily/weekly adherence trends, adherence changes over time, adherence comparisons to other relevant populations (e.g., all patients, patients on a particular rescue medication or controller medication or combination thereof, identification of triggers (spatial, temporal, environmental), rescue use trends over time, and rescue use comparisons to other relevant populations.

Figure 1B:
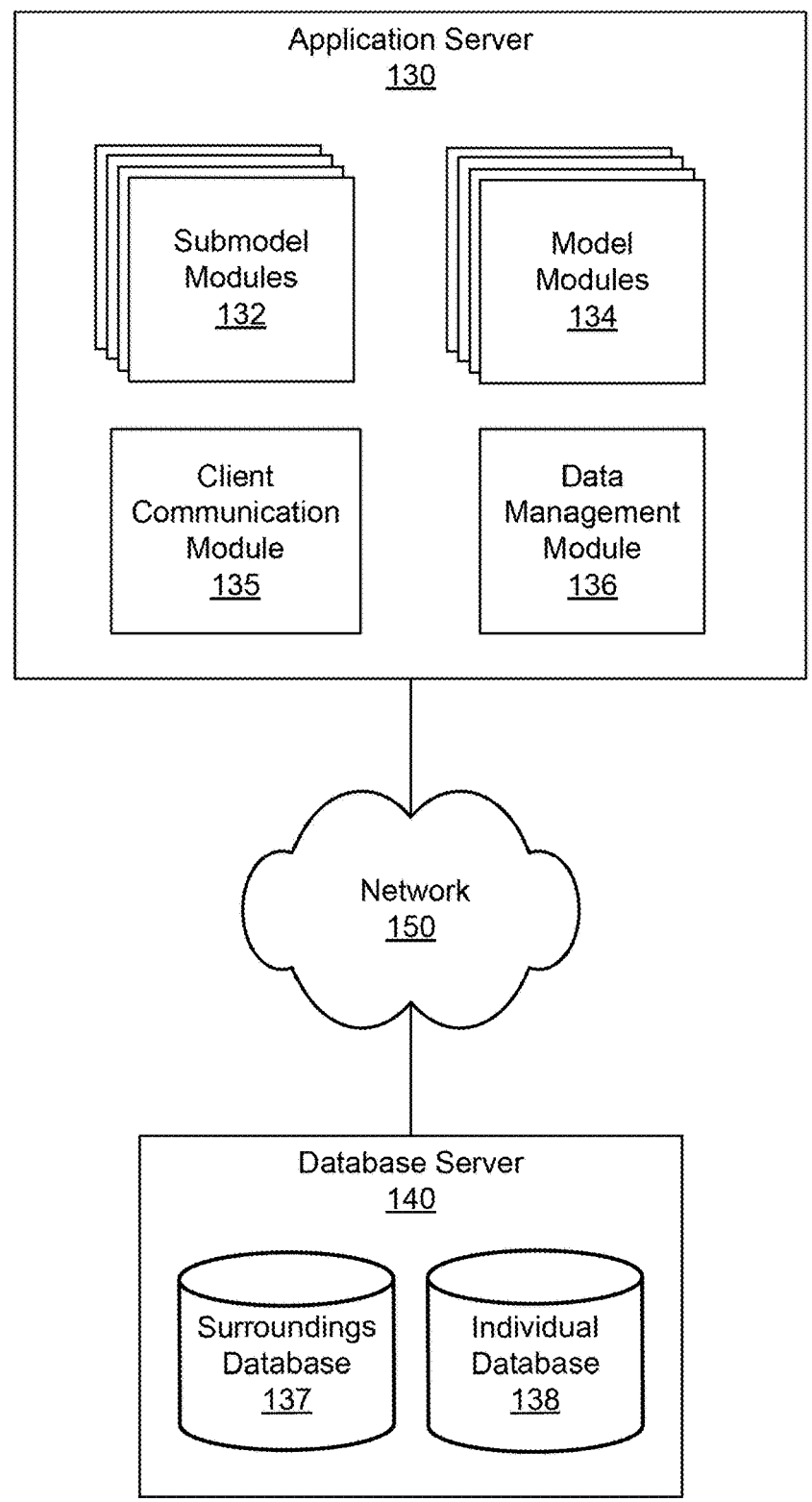
FIG. 1B shows an example application server and database server, according to one embodiment.

The application server 130 generates numerical estimates (also referred to as predictions) regarding respiratory disease risk, medicament device usage, and healthcare utilization for individuals and groups based on rescue medication event history and data received from data sources 180, including surroundings data and individual data. FIG. 1B shows an example application server 130 according to one embodiment. As shown in FIG. 1B, the application server 130 includes one or more submodel modules 132 and one or more model modules 134 for generating estimates. The submodel modules 132 and the model modules 134 are discussed in more detail below in Section V.

Responsive to any analyses performed, the application server 130 prepares and delivers push notifications to send to patients 111, authorized healthcare providers 112, and/or other users provided access to the patient's profile. Notifications can provide details about the timing, location, and affected patient(s) 111 involved in a medication rescue event. Notifications may additionally comprise a distress or emergency signal that requests emergency assistance that are distributed to emergency assistance providers 112.

In addition to providing push notifications, the server 130 may also provide pull notifications, for example at particular time intervals. Additionally, some notifications (regardless of type) may be triggered not in response to a particular event that has occurred to the patient, but in response to one of the underlying factors of an analysis performed by the server 130 changing. For example, if weather conditions indicate that an increase in air pollution is occurring or is imminent, this may trigger the carrying out of COPD risk analyses for all patients located in the particular geographic area where the pollution is occurring.

Notifications are provided through the network 150 to client applications 115 in a data format specifically designed for use with the client applications, and additionally or alternatively may be provided as short message service (SMS) messages, emails, phone calls, or in other data formats communicated using other communication mediums.

In addition to providing notifications to users, the application server 130 may provide notifications, analysis results, patient data, or surroundings data to external systems. External systems may include population health modules and information management systems such as electronic medical records (EMR) and electronic health records (EHR) systems.

I.D. Database Server

With respect to FIG. 1B, FIG. 1B shows an example database server 140 according to one embodiment. The database server 140 has a surroundings database 137 and an individual database 138 for storing data that is used as input data to the application server 130. The individual database 138 stores individual data, including patient and provider data related data such as profiles, medication events, patient medical history (e.g., electronic medical records). individual data is encrypted for security and is at least password protected and otherwise secured to meet all Health Insurance Portability and Accountability Act (HIPAA) requirements. Any analyses that incorporate data from multiple patients (e.g., aggregate rescue medication event data) and are provided to users is de-identified so that personally identifying information is removed to protect patient privacy.

The surroundings database 137 stores non-patient data used in analyses, referred to herein as surroundings data. Surroundings data includes regional data about a number of geographic regions such as public spaces in residential or commercial zones where patients are physically located and may be exposed to pollutants. Surroundings data may specifically include or be processed to obtain a patient's proximity to green space (areas including concentrated numbers of trees and plants) and proximity to different types of human organizations such as may be used to infer a patient's socioeconomic status. One example of regional data includes georeferenced weather data, such as temperature, wind patterns, humidity, the air quality index, and so on. Another example is georeferenced pollution data, including particulate counts for various pollutants at an instance of time or measured empirically. The regional data includes information about the current weather conditions for the time and place of the rescue event such as temperature, humidity, air quality index. Surroundings data may be historical data, current data or future data. Current data and historical data are measured or determined based on past or present conditions. Future data is predicted data for a particular time or time period in the future. Future data may be received from data sources 180 or determined from historical or current data stored in the surroundings database 137.

All of the items of data above may vary over time, and as such the data itself may be indexed by time, for example separate data points may be available by time of day (including by minute or hour), or over longer periods such as by day, week, month, or season. Input data is discussed in more detail below in Section V.A. Although the database server 140 is illustrated in FIGS. 1A and 1B as being an entity separate from the application server 130 the database server 140 may alternatively be a hardware component that is part of another server such as server 130, such that the database server 140 is implemented as one or more persistent storage devices, with the software application layer for interfacing with the stored data in the database is a part of that other server 130.

The database server 140 stores data according to defined database schemas. Typically, data storage schemas across different data sources vary significantly even when storing the same type of data including cloud application event logs and log metrics, due to implementation differences in the underlying database structure. The database server 140 may also store different types of data such as structured data, unstructured data, or semi-structured data. Data in the database server 140 may be associated with users, groups of users, and/or entities. The database server 140 provides support for database queries in a query language (e.g., SQL for relational databases, JSON NoSQL databases, etc.) for specifying instructions to manage database objects represented by the database server 140, read information from the database server 140, or write to the database server 140.

I.E. Network

The network 150 represents the various wired and wireless communication pathways between the client 110 devices, the sensor 120, the application server 130, and the database server 140. Network 150 uses standard Internet communications technologies and/or protocols. Thus, the network 150 can include links using technologies such as Ethernet, IEEE 802.11, integrated services digital network (ISDN), asynchronous transfer mode (ATM), etc. Similarly, the networking protocols used on the network 150 can include the transmission control protocol/Internet protocol (TCP/IP), the hypertext transport protocol (HTTP), the simple mail transfer protocol (SMTP), the file transfer protocol (FTP), etc. The data exchanged over the network 150 can be represented using technologies and/or formats including the hypertext markup language (HTML), the extensible markup language (XML), etc. In addition, all or some links can be encrypted using conventional encryption technologies such as the secure sockets layer (SSL), Secure HTTP (HTTPS) and/or virtual private networks (VPNs). In another embodiment, the entities can use custom and/or dedicated data communications technologies instead of, or in addition to, the ones described above.

II. Example Computing Devices

Figure 2:
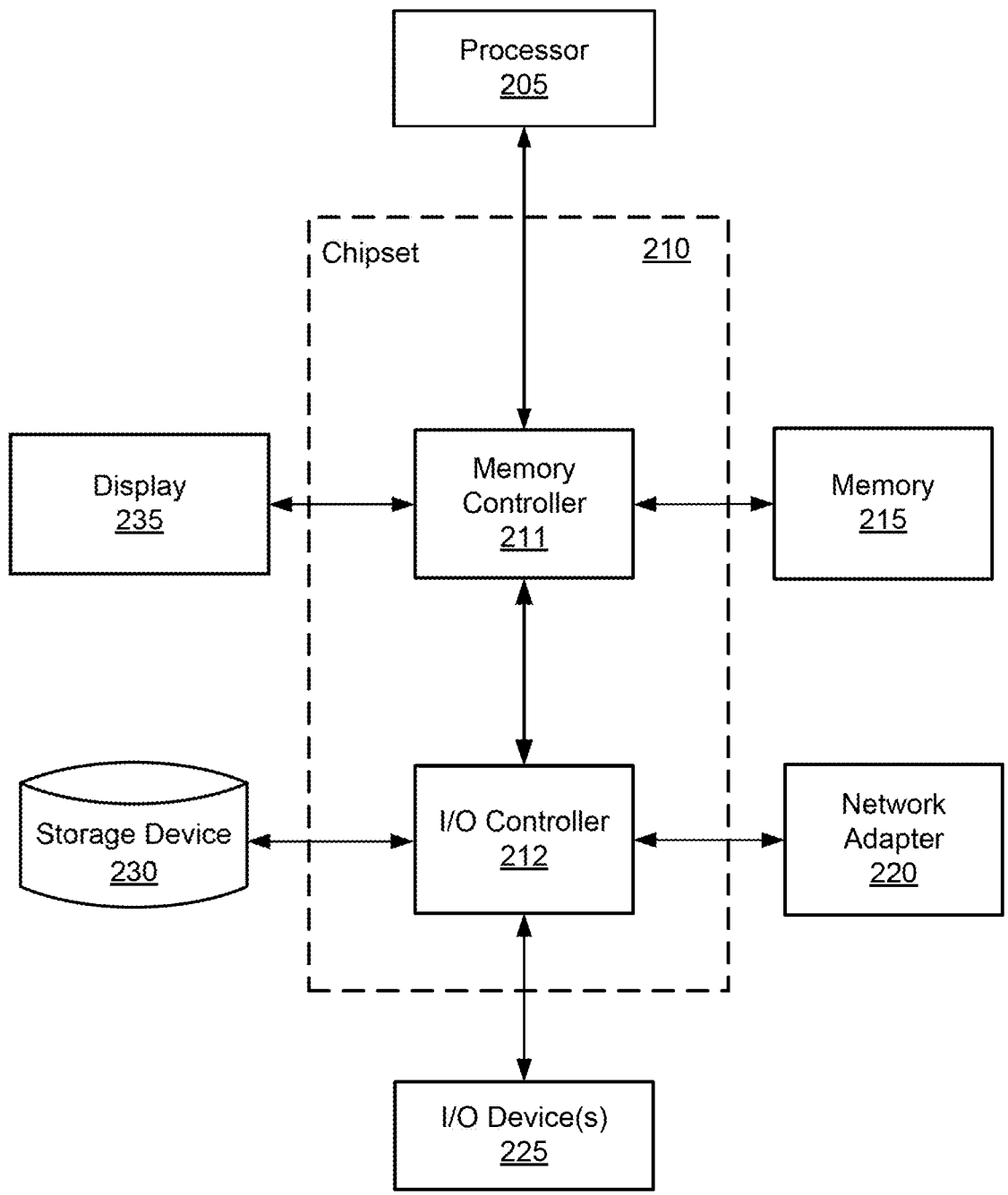
FIG. 2 is a high-level block diagram illustrating an example of a computing device used in either as a client device, application server, and/or database server, according to one embodiment.

FIG. 2 is a high-level block diagram illustrating physical components of an example computer 200 that may be used as part of a client device 110, application server 130, and/or database server 140 from FIG. 1A, according to one embodiment. Illustrated is a chipset 210 coupled to at least one processor 205. Coupled to the chipset 210 is volatile memory 215, a network adapter 220, an input/output (I/O) device(s) 225, a storage device 230 representing a non-volatile memory, and a display 235. In one embodiment, the functionality of the chipset 210 is provided by a memory controller 211 and an I/O controller 212. In another embodiment, the memory 215 is coupled directly to the processor 205 instead of the chipset 210. In some embodiments, memory 215 includes high-speed random access memory (RAM), such as DRAM, SRAM, DDR RAM or other random access solid state memory devices.

The storage device 230 is any non-transitory computer-readable storage medium, such as a hard drive, compact disk read-only memory (CD-ROM), DVD, or a solid-state memory device. The memory 215 holds instructions and data used by the processor 205. The I/O device 225 may be a touch input surface (capacitive or otherwise), a mouse, track ball, or other type of pointing device, a keyboard, or another form of input device. The display 235 displays images and other information from for the computer 200. The network adapter 220 couples the computer 200 to the network 150.

As is known in the art, a computer 200 can have different and/or other components than those shown in FIG. 2. In addition, the computer 200 can lack certain illustrated components. In one embodiment, a computer 200 acting as server 140 may lack a dedicated I/O device 225, and/or display 218. Moreover, the storage device 230 can be local and/or remote from the computer 200 (such as embodied within a storage area network (SAN)), and, in one embodiment, the storage device 230 is not a CD-ROM device or a DVD device.

Generally, the exact physical components used in a client device 110 will vary in size, power requirements, and performance from those used in the application server 130 and the database server 140. For example, client devices 110, which will often be home computers, tablet computers, laptop computers, or smart phones, will include relatively small storage capacities and processing power, but will include input devices and displays. These components are suitable for user input of data and receipt, display, and interaction with notifications provided by the application server 130. In contrast, the application server 130 may include many physically separate, locally networked computers each having a significant amount of processing power for carrying out the analyses introduced above. In one embodiment, the processing power of the application server 130 provided by a service such as Amazon Web Services™. Also in contrast, the database server 140 may include many, physically separate computers each having a significant amount of persistent storage capacity for storing the data associated with the application server.

As is known in the art, the computer 200 is adapted to execute computer program modules for providing functionality described herein. A module can be implemented in hardware, firmware, and/or software. In one embodiment, program modules are stored on the storage device 230, loaded into the memory 215, and executed by the processor 205.

III. Dashboard

Figure 3A:
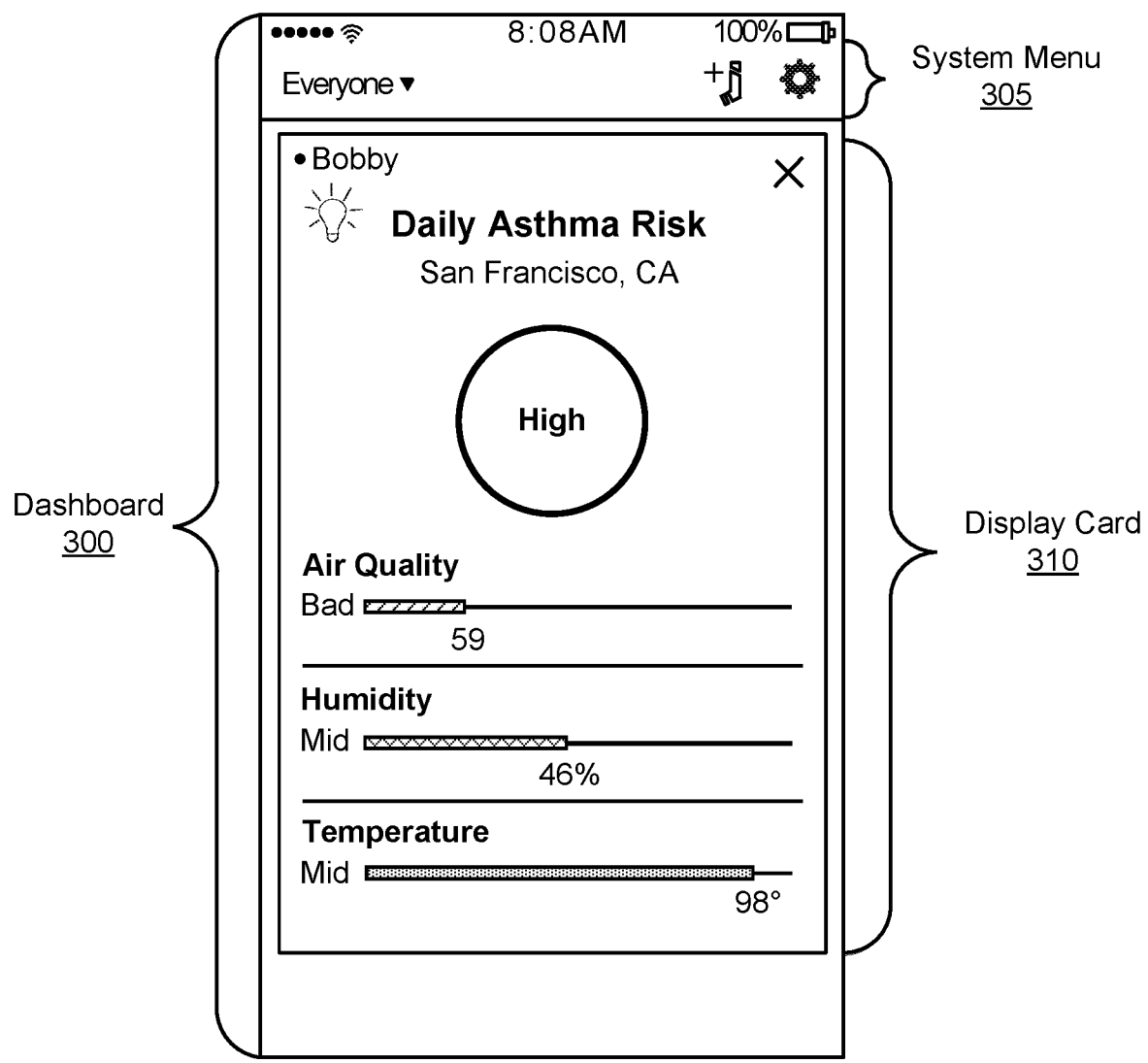
FIG. 3A shows a dashboard of a client application that allows a user to interact with an analytics system, according to one embodiment.

The dashboard, for example dashboard 300 illustrated in FIG. 3A, allows users to interact with the analytics system 100. The dashboard 300 provides a means to transfer information on a user-to-user (e.g., patient 111 to provider 112) or user-to-system/system-to-user basis. Dashboards 300 are accessed through the client application 115 on the client device 110 and provide a mechanism for both patients and healthcare providers to monitor medication rescue events, exchange personalized patient healthcare information, and received notifications. Patients may communicate with other health care provider and other patients through the dashboard 300, for example, to discuss and share information about their condition, medication usage, and management. The ability to share healthcare information may give patients or healthcare care providers experiencing a same issue a way to share individual perspectives.

The dashboard 300 also allows authorized health care providers 112 to access a list of patients to view, annotate, update, interact with, and export information about patient and community data and statistics in various demographics or geographic segments. Using the dashboard 300, healthcare providers are able to monitor patients individually or in aggregate, to receive and provide feedback (e.g. compliance reminders) on how their associated patient populations are responding to medication and condition management guidance. A healthcare provider who has access to individual or multiple patients has the ability to establish notification thresholds, set parameters for the notifications, and receive notifications when patients' event history matches certain conditions (e.g., a rescue event). Additionally, the dashboard 300 can receive and display regular reports of event patterns for specific demographic generated by the analytics system 100.

The dashboard 300 presents a variety of information including tabular data, graphical visualizations, and analyses to users through display "cards" 310. Display cards 310 are conformably suited to smaller displays typical of portable client devices 110, for example mobile phones or tablets, and include "bite size" pieces of information that mimic the organizational style found in baseball cards. The dashboard 300 may also include a system menu 305 that allows users to navigate through different categories of healthcare information.

Notifications provided by the application server 130 are related to the display cards 310. Generally, notifications include not only information to be presented to the user through the application 115, but also parameters for specifying which display card 310 is to be used to display the contents of the notification. Generally, any information pushed/pulled from the application server 130 may be associated with one or more cards. For example, a notification can be pushed to the patient based on the outcome of an analysis performed by server 130. The dashboard 300 will process the notification and determine which card/s to use to present the information in the notification. Continuing the example, the recipient of the notification may make a request (pull) data from the application server 130. The application server 130 provides the requested data in another notification, and the dashboard 300 then determines which display card 310 to display the requested information.

IV. Event Detection Process

As an initial step for generating notifications, a patient interfaces with the dashboard 300 to create a patient profile. Once the patient is finished completing their patient profile, the client device 110 transmits the patient profile for use by the application server 130 and storage by the database server 140. Once a patient's patient profile is initialized, the application server 130 may begin to receive medications events, including rescue medication events and controller medication events detected by the sensor 120 associated with the patient's medicament device 160.

Figure 4:
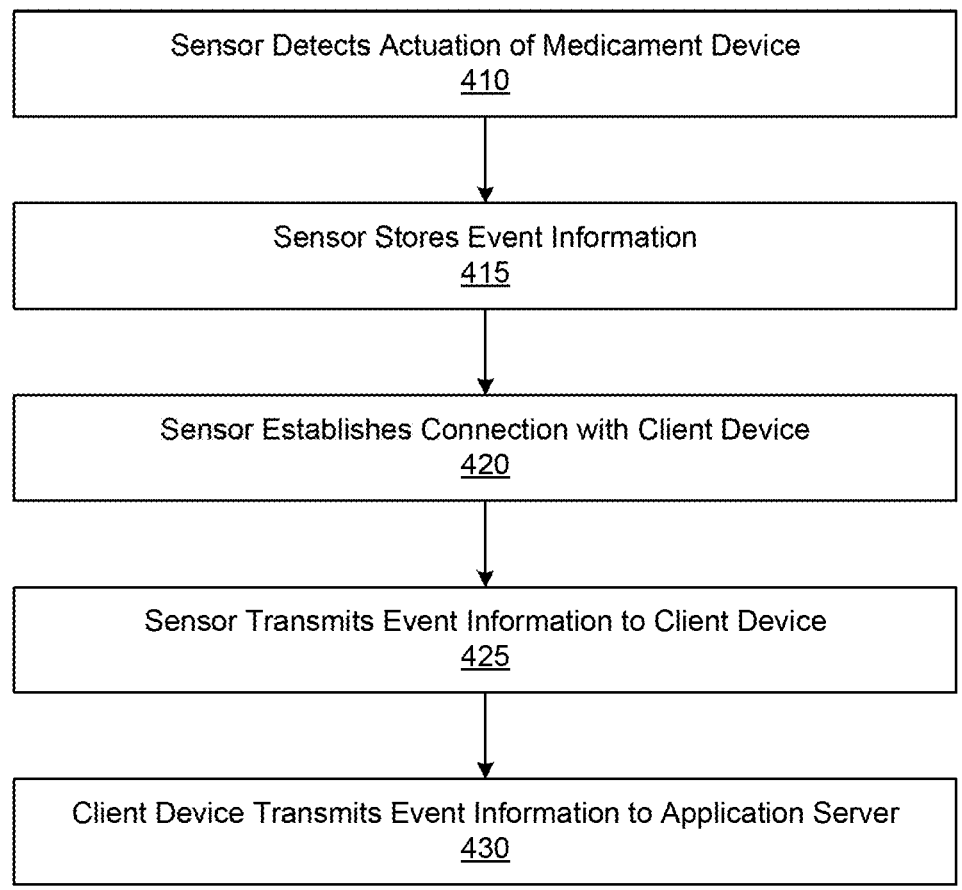
FIG. 4 shows a flowchart for detecting a medication event by an analytics system, according to one embodiment.

Referring now to FIG. 4, the application server 130 generally receives an event anytime the patient uses their rescue medicament device 160 to relieve difficulty breathing or other respiratory symptoms. As an example of the process for capturing such an event for a particular device 160/sensor 120 combination, at the start of symptoms, the sensor 120 may detect 410 an actuation of the rescue medicament device 160 consistent with the dispensing of medicament. The actuation indicates that an event has occurred.

After the event is detected, the sensor 120 is configured to store 415 data associated with the event in active memory of the sensor 120. The event data may include information that describes the time and date of associated with the event, the status or condition of the medicament device 160 (e.g. battery level), the number of doses of medication remaining (before or after the event), self-test results, and physiological data of a patient being treated with the medicament device 160 as measured by the sensor 120. As soon as the sensor establishes a network connection with either the client device 110 or network 150, the sensor transmits 425 any locally stored event data to the client device 110 or the application server 130. If the event data was transmitted to the client device 110 first, the client device 110 then transmits 430 the rescue event data to the application server 130 as soon as the client device 110 establishes a network connection with the network 150. Depending upon the implementation, either the client device 110 or sensor 120 will add the geographic location where the event took place to the event data transmitted to the application server 130.

V. Predicting Respiratory Disease Risk and Medicament Device Usage

One type of analysis performed by the application server 130 is predicting, using models, respiratory disease risk, medicament device usage, exacerbations, and healthcare utilization for individuals and groups. Model outputs may be used to provide information to patients, family members, healthcare providers, information management systems, and other interested parties. Model applications are discussed in more detail below in Section V.C.

Figure 5:
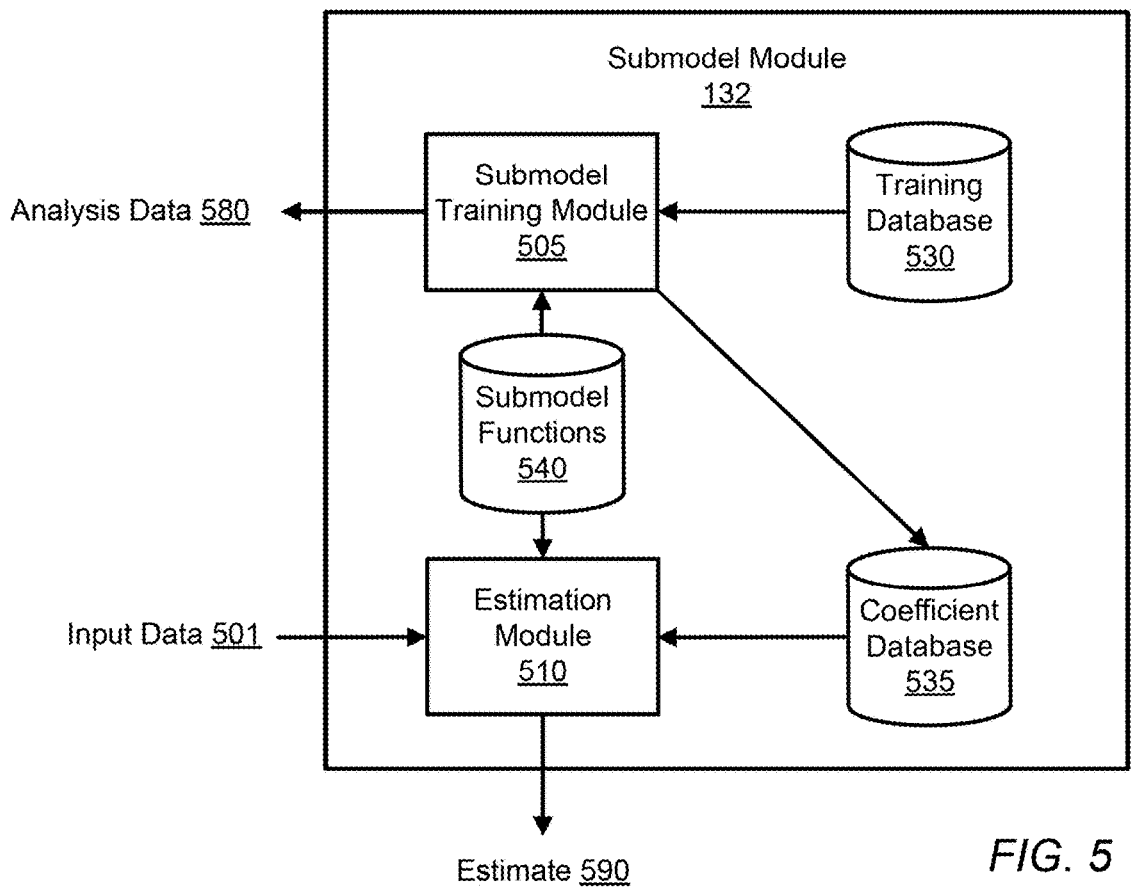
FIG. 5 shows an example submodel module including arrows indicating the flow of data, according to one embodiment.
Figure 6:
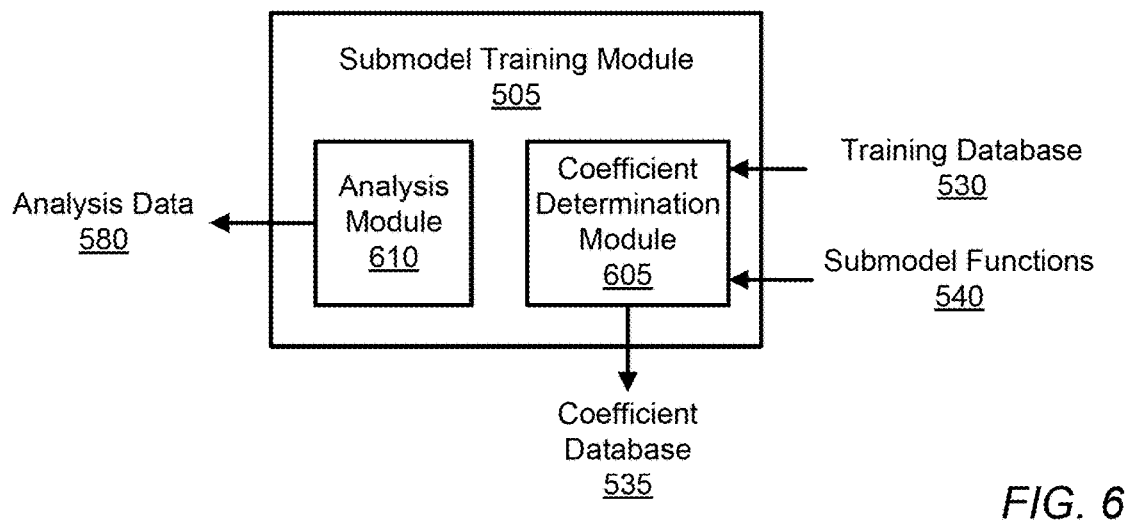
FIG. 6 shows an example submodel training module including arrows indicating the flow of data, according to one embodiment.

The models are comprised of one or more trained submodels that generate estimates of respiratory disease risk, medicament device usage, exacerbation, and healthcare utilization. FIG. 5 shows an example submodel module 132 including arrows indicating the flow of data, according to one embodiment. The submodel module 132 includes a submodel training module 505, an estimation module 510, a training database 530, a coefficient database 535, and submodel functions 540. The submodel receives input data 501 from the database server 140 and generates estimates 590 and analysis data 580. FIG. 6 shows an example submodel training module 505, including arrows indicating the flow of data, according to one embodiment. The submodel training module 505 includes a coefficient determination module 605 and an analysis module 610.

Submodel estimates 590 may be specific to an individual (individual estimates) or may apply to groups of individuals with common characteristics such as geographical location or respiratory disease risk score (aggregate estimates). Models may use individual estimates, aggregate estimates, or both to generate outputs. The submodels take as inputs at least one of surroundings data from surroundings database 137 and individual data from individual database 138. Input data is discussed in more detail below in Section V.A.

Submodels are trained using training data. Submodel training data includes collected data regarding detected events as well as input data that corresponds to the collected data. In one embodiment, submodel training data is stored in the training database 530. Submodel training is discussed in more detail below in Section V.B. with respect to FIGS. 5 and 6.

V.A. Input Data

Input data is data that is used to generate model estimates. Input data may be received from many sources. Different types of input data include surroundings data from surroundings database 137 and individual data from individual database 138. Input data used to determine a particular submodel estimate 590 may include many different types of data received from different data sources. Input data is also used as training data along with usage event data, exacerbation data, healthcare utilization data, and other patient data to determine model parameters such as regression coefficients.

Input data may be constant (i.e., not time dependent) or it may vary over time. As such the data itself may be indexed by time, for example separate data points may be available by time of day (including by minute or hour), or over longer periods such as by day, week, month, or season. Input data that varies over time (e.g., meteorological data and air quality data) may be collected at regular intervals and may include a timestamp. The submodels may use timestamps to generate estimates that are time-dependent. For example, one submodel may estimate immediate medicament device usage probability for an individual while another estimates time-lagged medicament device usage probability for an individual.

Input data stored in the database server 140 or made available to the application server 130 may be in raw form as actual values or in a relative form as a value relative to other data. Examples of input data in raw form include data with standard units (e.g., wind speed values in miles per hour, $NO_2$ in parts per billion, etc.). Examples of input data in relative form include interquartile range (IQR) values, rate ratio (RR) values, and confidence intervals (CI). IQR is a measure of statistical dispersion, being equal to the difference between the upper and lower quartiles. RR is a relative difference measure used to compare the incidence rates of events. CI is a range of values defined such that that there is a specified probability that the value of a parameter lies within it. For example, the submodel training module 505 may determine rate ratios in interquartile range increments and corresponding 95% confidence intervals to identify the degree of impact of various types of input data from databases 137 and 138 introduced above on medicament device use. Rate ratios in IQR increments and 95% CI may be used to represent the relative impacts of input on medicament device use. Expressing input data in relative form improves the computational efficiency of models by limiting the range of inputs and outputs. Further, expressing input data in relative form makes comparison of model coefficients with each other easier, which can, for example, make it easier to determine the degree to which input variables are predictive with respect to models. Model coefficients are discussed in more detail below with respect to Table 4 and Section V.B.

V.A.1 Surroundings Data

Surroundings data is data about a geographical area, and is used for individual and aggregate estimates. Surroundings data includes, for example, environmental and land use data, census and neighborhood data, meteorological data, and air quality data. Surroundings data may be received from many different data sources, and is stored in the surroundings database 137. Table 1 includes example data sources for surroundings data. Table 2 includes example surroundings data and example units for the data.

TABLE 1

Data Sources for Surroundings Data

| Data Source Category | Example Data Sources |
| --- | --- |
| Environmental and Land Use Data | California's Pesticide Use Reporting database<br>Industrial Land Use Layers<br>Industrial emission release points (by government permits)<br>Highway network<br>Major roadway network<br>Local roadway network<br>Railroad network<br>Traffic count (Average Annual Daily Traffic)<br>National Land Cover Dataset (NLCD)<br>Ecoregions<br>Property Assessment spatial data<br>Land use spatial data<br>Zoning assignments<br>Parks and recreation areas<br>Natural Areas |
| Census and Neighborhood Data | Census block group layer<br>Census tract layers<br>Zip code layers<br>County boundary layer<br>Metropolitan area layers |
| Meteorological Data | Mesonet weather observation points<br>Wind MesoMap model output (vector)<br>Wind MesoMap model output (grid)<br>Climate Data from PRISM |
| Air Quality Data | Air pollution monitoring locations (Environmental Protection Agency)<br>Fixed site saturation monitoring (gaseous pollutants NO, NO2, NOx, CO, SO2, O3 and particles PM1, PM2.5, PM10 and pollen)<br>Mobile saturation monitoring (gaseous pollutants NO, NO2, NOx, CO, SO2, O3 and particles PM1, PM2.5, PM10 and pollen).<br>Modeled Airsheds<br>UCD/CIT (University of California Davis/California Institute of Technology) Source Oriented Chemical Transport models. |

TABLE 2

Surroundings Data Examples

| Category | Example Data Types | Units |
| --- | --- | --- |
| Environmental and Land Use Data | Traffic count (Average Annual Daily Traffic) | Cars/trucks per day at specific counting site |
| | Distance to airports | Miles |
| | Distance to mines | Miles |
| | Distance to large pollution sources | Miles |
| | Distance to other pollution sources | Miles |
| | Distance to railroad | Miles |
| | Distance to railyard | Miles |
| | Distance to highways | Miles |
| | Distance to major roadways | Miles |
| | Distance to local roadways | Miles |
| | Natural features | Hectares or Percentage |
| | Topography (DEM) | Feet above sea level |
| | US elevation (National Elevation Dataset) | Feet above sea level |
| | Pesticide use records | Pounds applied of pesticide type |
| | Chemical volatility (i.e. vapor pressure) | Pa (Pascals) or mmHg (millimeters of mercury). |
| | Chemical use classification | e.g. insecticide, herbicide |
| | Chemical mode of action | e.g., volatile, stable |
| | Method of pesticide application | ground or aerial application |
| | Tree Canopy Closure | Percentage |
| | Normalized Difference Vegetation Index (NDVI) Greenness | Between −1 and 1, no unit |
| | NDVI duration | Between −1 and 1, no unit |
| | NDVI amplitude | Between −1 and 1, no unit |
| | NDVI end of season | Between −1 and 1, no unit |
| | NDVI max | Between −1 and 1, no unit |
| | NDVI start of season | Between −1 and 1, no unit |
| | NDVI time integrated | Between −1 and 1, no unit |
| | NDVI time of maximum | Between −1 and 1, no unit |

TABLE 2-continued

Surroundings Data Examples

| Category | Example Data Types | Units |
|---|---|---|
| | NLCD percent impervious surface | Percentage |
| | Commercial (%) | Percentage |
| | Condominium (%) | Percentage |
| | Farm (%) | Percentage |
| | Utility & railroad (%) | Percentage |
| | Industrial (%) | Percentage |
| | Residential (%) | Percentage |
| | Exempt Properties (significant associations only) | Percentage |
| | Educational (%) | Percentage |
| | Metro Government sites (%) | Percentage |
| | Religious (%) | Percentage |
| | State Government sites (%) | Percentage |
| | Residential Condo | Percentage |
| | Master Lot (%) | Percentage |
| Census and Neighborhood Data | Census block group | Group ID |
| | Census tract | Tract ID |
| | Zip code | Zip code |
| | County | County name |
| | Metropolitan Area | Metro area name |
| | Household density | Households per geographic unit |
| | % Adults with high school diploma | Percentage |
| | % population below 50% poverty level | Percentage |
| | Median household income | Dollars per year |
| | Average household income | Dollars per year |
| | Per capita income | Dollars per year |
| | Households with income below poverty level | Number or percentage |
| | Household ownership | Number or percentage |
| | Median home values | Dollars |
| | Renter households | Number or percentage |
| | Median year structure built | Year |
| | Households receiving food assistance (SNAP) | Number or percentage |
| | Percent Population below 50% Poverty Level | Percentage |
| | Race/ethnicity composition | Percentage of each racial/ethnic group |
| | % with education > grade 9 | Percentage |
| | % of population 100-199% of poverty level | Percentage |
| | % of population > 200% of poverty level | Percentage |
| | Year built | Year |
| | Basement presence | Yes/No |
| | Number of fireplaces | Number |
| | Presence of central air | Yes/No |
| | Number of baths | Number |
| | Number of bedrooms | Number |
| | Type of property | e.g., residential, commercial |
| | Total property value | Dollars |
| | Property size | Square feet |
| | Multi-family or single-family | Multi- or single- |
| | Total Crime Index | Count of number of different types of crimes committed annually per geographic unit |
| | Personal Crime Index | Count of number of crimes committed annually per geographic unit |
| | Murder Index | Count of number of crimes committed annually per geographic unit |
| | Rape Index | Count of number of crimes committed annually per geographic unit |
| | Robbery Index | Count of number of crimes committed annually per geographic unit |
| | Assault Index | Count of number of crimes committed annually per geographic unit |
| | Property Crime Index | Count of number of crimes committed annually per geographic unit |

TABLE 2-continued

Surroundings Data Examples

| Category | Example Data Types | Units |
|---|---|---|
| | Burglary Index | Count of number of crimes committed annually per geographic unit |
| | Larceny Index | Count of number of crimes committed annually per geographic unit |
| | Motor Vehicle Theft Index | Count of number of crimes committed annually per geographic unit |
| Meteorological Data | Relative Humidity (Daily)/Dew point temperature | Percentage |
| | Temperature (hourly) | Degrees |
| | Temperature high (daily) | Degrees |
| | Temperature low (daily) | Degrees |
| | Precipitation (daily) | Inches |
| | Wind direction (hourly) | Direction or degrees |
| | Wind speed (hourly) | Miles per hour |
| | Ambient air temperature (hourly) | Degrees |
| | Surface temperature | Degrees |
| Air Quality Data | NOX (daily, hourly, minute) | Parts per billion |
| | Ozone (daily, hourly, minute) | Parts per million |
| | PM10 (daily, hourly, minute) | Micrograms per cubic meter |
| | PM2.5 (daily, hourly, minute) | Micrograms per cubic meter |
| | PM2.5 - Percentage of Days Above Average, by Tract | Percentage |
| | SO2 (daily, hourly, minute) | Parts per million |
| | CO and CO2 (daily, hourly, minute) | Parts per million |
| | Air Quality Index (daily) | No units |
| | Pollen (grass, weed, flower, tree) | Counts |
| | Mold spore counts | Counts |
| | Criteria pollutants non-attainment areas | Hectares or percentage |
| | Non-attainment areas for lead | Hectares or percentage |
| | Ozone non-attainment areas | Hectares or percentage |
| | PM 2.5 non attainment areas | Hectares or percentage |
| | Hourly estimated components of aerosols, at spatial resolution of 1-4 km, These data include particle mass, daily concentrations of 11 species and 8 sources of primary and secondary particles. | Micrograms per cubic meter |

In various embodiments, surroundings data is received from one or more data sources 160 and stored in the database server 140 until it is ready for use by the models. Air quality data may be received from the U.S. Environmental Protection Agency's (EPA) Air Quality System (AQS) for the following criteria pollutants: Nitrogen Dioxide ($NO_2$), Ozone ($O_3$), Sulfur Dioxide ($SO_2$), and Particulate Matter (PM) with aerodynamic diameter≤2.5 μm ($PM_{2.5}$) and ≤10 μm ($PM_{10}$). Air Quality Index (AQI) data is received from available monitoring stations. AQI is an index of daily ambient concentrations of up to five criteria air pollutants (i.e., $O_3$, PM, Carbon Monoxide, $SO_2$ and $NO_2$). It is a piecewise linear function of a pollutant concentration and it ranges from less than 50 (good air quality) to over 400 (poor air quality). If multiple pollutants are measured at a monitoring site, then the highest pollutant level is reported for AQI at that location. The AQS pollutant data are collected at different temporal resolutions, including: hourly concentrations for $NO_2$ and $SO_2$, daily concentrations for $PM_{2.5}$ and $PM_{10}$, a daily mean of 8 hour maximum for $O_3$, and mean daily values for AQI.

Air quality data may also be received from sources that perform air quality monitoring outside of the standard compliance monitoring network (e.g., EPA AQS data). For example, a network of outdoor fixed site air quality monitors may measure the main pollutants in a region, including NO2, NO/NOX, PM1, PM2.5, PM10, CO, O3, and SO2. The fixed site monitors may measure pollutant concentrations for an entire year with a sampling interval of 5 minutes. Additionally, pollen may be measured at multiple sites at an interval of one hour. The fixed site monitor locations may be determined using a location-allocation algorithm to optimize network coverage.

Air quality data may also be collected using mobile monitoring equipment. Mobile monitoring may be performed at various times throughout the year to account for seasonal changes in pollution. A sample mobile monitoring approach travels multiple routes, with each route being traveled five times clockwise and four times counter clockwise in seasons 1 and 3 (e.g., winter and summer), and four times clockwise and five times counter clockwise in seasons 2 and 4 (e.g., spring and fall). In each season, each route is traveled six times per day on weekdays and three times per days on weekend days, resulting in a total of 108 mobile runs for a year. The mobile sampling interval may be based on time (e.g., every 30 seconds) or based on distance (e.g., every 100 feet).

Air quality data may further include indoor air quality data. For example, air quality monitors may be deployed inside participants' homes. Housing characteristics determined from property assessment data, race-ethnicity data, and the like, may be used to determine indoor air pollution sources, as well as to select households for balanced indoor air quality sampling and rotation of sampling from one season to another. The measured indoor air quality may be integrated with outdoor air quality to derive infiltration coefficients based on housing characteristics and race-ethnicity information. These coefficients may be used to derive indoor air quality for those homes of the participants without indoor air quality monitoring.

In one embodiment, the data management module 136 uses an inverse distance-weighting (IDW) algorithm to estimate pollutant concentrations for locations of medicament device use per hour or per day using the AQS monitoring data. The spatially-interpolated daily values are used to represent hourly measures of pollutants when only daily data were available. The concentration of a pollutant at location j of medicament device use during hour t is calculated using all known monitoring sites (1=1, 2, . . . , n) concentration measurements ($c_{ijt}$):

$$c_{jt} = \sum_i (w_{ij} * c_{ijt}) / \sum w_{ij} \quad \text{(Equation 1)}$$

where $w_{ij} 1/d_{ij}$ and $d_{ij}$ is the distance between known monitoring station i and medicament device use location j. Thus, for any given rescue event, a concentration measurement ($c_{ijt}$) can be determined for one more hours t at the location of the event j for one more known monitoring sites. For medicament device use events without location data, daily or hourly regional mean statistics are used.

In one embodiment, pollution concentrations at a given location and time are predicted using land use regression (LUR) techniques. LUR predicts pollution concentrations at a given location based on surrounding land use, traffic and other characteristics. Typically, LUR assumes linear relationships between predictors and air pollutant concentrations. For example, a D/S/A LUR algorithm assumes the existence of a non-linear (e.g., polynomial) relationship between pollutant concentrations and some predictors. Thus, polynomial functions may be included in the models. This may create a situation in which a higher-ordered term for a variable predicts a different association than a lower-ordered term, which reflects conditional mean-effects and represents a non-linear relationship between the predictor and the pollutant concentrations.

In V-fold cross-validation, such as those implemented in D/S/A LUR modeling frameworks, the original sample is randomly partitioned into V (the number of folds) equal size subsamples. Of the V subsamples, a single subsample is retained as the validation data for testing the model, and the remaining V−1 subsamples are used as training data. The cross-validation process is then repeated V times, with each of the V subsamples used exactly once as the validation data. The V results from the folds can then be averaged (or otherwise combined) to produce a single estimation. The advantages of this method over leave-one-out cross-validation are that (1) the prediction errors are less impacted by a single outlier, (2) compared to repeated random sub-sampling, all observations in the V-folds are used for both training and validation, and (3) each observation is used for validation exactly once. Since each time an independent validation dataset is used to assess the performance of a model built using a training dataset, the V-fold cross-validation implemented in D/S/A minimizes the chance of over-fitting the model to the data.

Pollen data may be received from local monitoring stations that include counts for mold spores, and tree, grass and weed pollen. If the data is limited to a daily count, all the medicament device use events on a specific day are assigned the same pollen and mold counts. In other embodiments, pollen data are collected from the National Allergy Bureau of the American Academy of Allergy Asthma & Immunology, POLLEN.COM or other sources.

Meteorological data, including wind speed, relative humidity, temperature and atmospheric pressure, may be received from EPA AQS sites. The IDW algorithm assigns daily meteorological conditions for the medicament device use locations. In other embodiments, meteorological data such as daily precipitation, snow and wind direction data are received from the National Oceanic and Atmospheric Administration (NOAA). Wind direction data (0-360°) are reclassified into eight categories: north, northeast, east, southeast, south, southwest, west and northwest.

Land use and property data may be received from local information sources (e.g., the Louisville/Jefferson County Information Consortium for 2014). For each medicament device use location, corresponding land use characteristics (e.g., what percent of the land area where the event took place is residential) the data management module 136 calculates within a 250 meter buffer, an area representing local influence on an individual. In one embodiment, land cover data is received from the National Land Cover Database at a spatial resolution of 30 meters. The land cover classes for vegetation include forest (deciduous, evergreen and mixed), shrub land, and grassland/herbaceous cover. The primary interest in including land cover is to examine the potential protective (e.g., reductions of air pollution by tree) or causal (e.g., pollen generation by weed) effect of vegetation on medicament device use. Pollen counts are measured at the regional level and are temporally resolved (daily) while land cover vegetation classification data are spatially resolved using the 250-meter buffer.

V.A.2 Individual Data

Individual data is data about an individual, and includes, for example, demographic data, socioeconomic data, health status data, exposure data, exacerbation data, and healthcare utilization data. Individual data is used to determine personalized estimates for patients or other persons. Individual data may be collected from patients, family members, providers, or other parties, and may be stored in the individual database 138.

For each patient, the application server 130 tracks the patient's start date, end date and active days in between during which the patient is actively tracking their medication use. For each medication use, the application server 130 receives the type of medication, the date, time, number of actuations, transmitting device type, and location for those participants with a smartphone device. Patients can also self-report on perceived symptoms, triggers, and whether the medicament device use was preemptive. The application server 130 additionally receives individual-level demographic, socioeconomic and health data. These data include, but are not limited to, those in Table 3.

TABLE 3

Example Individual Data Categories and Examples

| Category of individual-level data | Specific examples |
|---|---|
| Demographics | race/ethnicity, gender, age, date of birth |
| Socioeconomic status | education, income, employment, insurance carrier/type |
| General health characteristics | BMI, height, weight, blood pressure, respiratory rate, heart rate, comorbidity, smoking history, depression, historical healthcare utilization and pharmacy records, workplace exposures, |
| Respiratory disease characteristics | asthma control measured by the Asthma Control Test and the Propeller control score, sensor-collected controller medication adherence, peak flow and forced expiratory volume, asthma self-management and self-efficacy scores, quality of life, goals, asthma action plan, other health behaviors, perceived triggers and symptoms |
| COPD characteristics | GOLD grade, COPD Assessment Test score, smoking history, comorbidity, sensor-collected controller medication adherence, peak flow and forced expiratory volume, self-management and self-efficacy scores, quality of life, goals, other health behaviors, perceived triggers and symptoms |
| medicament device use | start date, end date and active days the participant is recording their medicament device use, and locations of medicament device use |
| Asthma and COPD healthcare utilization | emergency department visits, hospitalizations, systemic corticosteroids and other medication prescriptions |
| Exacerbations | Severe asthma exacerbations (events that require urgent action on the part of the patient and physician to prevent a serious outcome, such as hospitalization or death from asthma), Moderate asthma exacerbations (events that are troublesome to the patient, and that prompt a need for a change in treatment, but that are not severe; clinically identified by being outside the patient's usual range of day-to-day asthma variation. |
| Neighborhood characteristics (census-derived) | education level, demographics, income, rent vs. own property composition, respiratory disease prevalence and utilization costs, smoking and obesity prevalence |
| Home-based exposures (based on address) | home value, home age, pet ownership, wood or cooking smoke, second-hand cigarette smoke, central air, fireplaces |
| Workplace-based exposures (based on work address) | zoning and land use class, presence of exposures, |
| User Data | Number of active users, User locations |

V.B. Submodel Functions, Training, and Use

With reference to FIG. 1A, as introduced above, the submodels of the application server 130 generate individual or aggregate estimates of medicament device usage and respiratory disease risk for use in models. The submodels generate an estimate using one or more submodel functions based on input data and previously trained submodel coefficients. Submodel coefficients are determined during submodel training. Each submodel is trained using collected data and corresponding input data to determine the submodel coefficients. Submodel coefficients may, for example, be regression coefficients, however the exact form of the coefficients varies by submodel. Submodel coefficients may be expressed as raw values or relative values like RR, IQR or CI.

With reference to FIG. 5, FIG. 5 shows an example submodel module 132 for training and using a submodel. Training data for training the submodel is stored in the training database 530. The training database 530 may be a separate database, or it may simply refer to certain items of data from databases 137-138, such as historical medicament device usage events or other historical individual data and historical surroundings data. Submodel functions are stored in submodel functions store 540. Generally, these are static, however they may be updated from time to time by system administrator of system 130, or by specific users such as healthcare providers.

The submodel training module 505 determines submodel coefficients using training data and submodel functions. Submodel coefficients are stored in the coefficient database 535 and used by the estimation module 510 to generate estimates using submodel functions and input data. In various embodiments, the data management module 136 preprocesses input data, for example by computing time- or location-based averages, converting non-numerical variables to numerical representations, and the like. Some examples of this preprocessing are described in Section V, for example the IDW algorithm for determining concentration measurements $c_{ijt}$ at the location and time of a rescue event.

With reference to FIG. 6, FIG. 6 shows an example submodel training module 505 according to one embodiment. Generally, training a submodel includes identifying predictors, or types of input data, that impact medicament device use. The coefficient determination module 605 determines values for submodel coefficients for submodel functions 540 using training data from the training database 530. In one embodiment, submodel training is performed using maximum likelihood estimation, which entails finding the set of submodel coefficients and their values that best fit the training data 530 by maximizing one or more likelihood functions. Submodel coefficients are stored in the coefficient database 535.

Those submodel coefficients determined to be particularly impactful on medicament device use can be labeled as predictors for use and presentation as an output of the module 132 along with the estimates 590. To do this, the analysis module 610 of the submodel training module 505 generates analysis data 580 (the predictors) by performing statistical analysis on the trained submodel coefficients. Statistical operations may include determining statistical significance and association values for various input data types by comparing the relative predictiveness of different types of input data. Analysis data 580 may be used by model modules 134 to provide information about the predictiveness of various types of input data as model outputs.

Table 4 shows an example model output 580 that provides information about predicting rescue events from input data. The Predictor columns include various types of input data. The Association columns provide the direction of association with inhaler usage, where a positive association indicates that a higher measured input value is correlated with increased inhaler use, and a negative association indicates that a higher measure input value is correlated with decreased inhaler use. The significance values provide a measure of the magnitude of the predictiveness of each type of input data. Significance values and association values can be combined to give a magnitude and direction of predictiveness. Thus, in some embodiments, the submodel output may be data determined from the submodel coefficients after training, such as predictiveness of various types of input data relative to others. The example of Table 4 could be used by patients, providers, researchers and the like to understand both nominal measures of predictiveness for the input data as well as relative measures of predictiveness. The input data for the example of Table 4 was collected for the Louisville, Ky. area. Other models may take data from different geographic areas, and have different outputs that apply to those areas. Still other models may use data collected from various groups (e.g., age ranges, genders, socioeconomic groups, demographic groups, etc.) and have outputs that apply to those groups. As a result, model outputs may not only be compared within a single set of input data, but across different sets of input data to gain further insights.

TABLE 4

Example Determined Impact of Input Data Types

| Predictor (mean daily value) | Association with inhaler usage/day | sig. (p-value) |
|---|---|---|
| Air Pollution | | |
| PM$_{2.5}$ (μg m$^{-3}$) | + | . |
| PM$_{10}$ (μg m$^{-3}$) | + | *** |
| NO$_2$ (ppb) | + | * |
| O$_3$ (8-hr mean, ppm) | − | *** |
| SO$_2$ (ppm) | + | . |
| AQI | + | *** |
| Pollen | | |
| Grass (counts) | − | * |
| Weed (counts) | + | *** |
| Tree (counts) | − | *** |
| Mold (counts) | + | *** |
| Meteorological Condition | | |
| Pressure (millibars) | − | ** |
| Relative humidity (%) | + | . |
| Temperature (° F.) | + | *** |
| Wind Speed (knots) | − | * |
| Wind Direction (S) | + | ** |
| Land Use Type | | |
| Commercial (%) | + | . |
| Condominium (%) | − | . |
| Exempt (%) | + | *** |
| Farm (%) | + | . |
| Utility & railroad (%) | + | *** |

TABLE 4-continued

Example Determined Impact of Input Data Types

| Predictor (mean daily value) | Association with inhaler usage/day | sig. (p-value) |
|---|---|---|
| Industrial (%) | − | *** |
| Residential (%) | − | *** |
| Exempt Properties (significant associations only) | | |
| Educational (%) | + | ** |
| Metro Gov. (%) | + | *** |
| Religious (%) | + | *** |
| State Gov. (%) | − | *** |
| Residential Condo | + | *** |
| Master Lot (%) | | |

Notes:
Significance codes:
'***' 0.001
'**' 0.01
'*' 0.05
'.' 0.1
' ' >0.1;
"+" and "−" indicate respective positive and negative associations.
Each bivariate relationship is a negative binomial modeling result in which the number of active participants at a day was used as an offset. The wind direction refers to the south wind. Eight wind directions were considered including north (N), northeast (NE), east (E), southeast (SE), south (S), southwest (SW), west (W) and northwest (NW). Pollen from grass, weed and tree and mold are counts of spores of respective origin. AQI indicates how clean or polluted the air is and what associated health effects might be a concern. For definition of AQI, please refer to EPA website http://www.airnow.gov/ for detail.

V.B.1 Unadjusted Zero-Truncated Negative Binomial Submodels

One type of submodel uses an unadjusted zero-truncated negative binomial logistic regression to generate aggregate numerical estimates of events including medicament device usage, exacerbations, and healthcare utilization. These numerical estimates may be immediate, meaning the estimated number or probability of immediate events (e.g., in the next 20 minutes), or time-lagged, meaning the estimated number or probability of events at a later time (e.g., in the next 3 days). Time-lagged estimates identify the impacts of time-lagged exposures on respiratory disease exacerbations.

An example submodel function 540 that uses this type of regression is given by:

$$\log(E(Y_i)) = \beta_0 + \beta_1 * X_i + \log(A_i) + \varepsilon_i \quad \text{(Equation 2)}$$

where $E(Y_i)$ is the expected number of medicament device use events at the $i^{th}$ day in the future. $\beta_0$ and $\beta_1$ are submodel coefficients determined during submodel training, for example using maximum likelihood estimation. Using a negative binomial models such as this can be advantageous in determining a risk (numerical estimate) of a rescue inhaler usage event because rescue inhaler use data are highly over-dispersed, with the variance about 10 times the mean.

Input data for this type of submodel includes variables based on the input data from databases 137 and 138 discussed above in Section V.A. $X_i$ is an environmental predictor, which is a numeric representation of the input data. $X_i$ may be a single value or it may be a vector or matrix to represent multiple measurements of the same predictor or measurements of multiple predictors. Further, the values of $X_i$ may be relative values (e.g., RR, IQR, CI, etc.) or raw values. An example environmental predictor vector $X_i$ with relative values is below:

$$\begin{bmatrix} \text{Tree Pollen} \\ \text{Grass Pollen} \\ \text{Mold Pollen} \end{bmatrix} = \begin{bmatrix} 0.21 \\ 0.45 \\ 0.66 \end{bmatrix}$$

where the values for each type of pollen are presented as rate ratios (relative values) as opposed to pollen counts (raw values). This allows the input values to be comparable to one another, and it also causes the output coefficients $\beta_0$ and $\beta_1$ to be comparable to one another as well. Example coefficients $\beta_0$ and $\beta_1$ are below:

$$\beta_0 = \begin{bmatrix} 34.2 \\ 45.5 \\ 16.7 \end{bmatrix} \quad \beta_1 = \begin{bmatrix} 0.56 \\ 0.02 \\ -0.4 \end{bmatrix}$$

Further, $A_i$ is the total number of active participants at the $i^{th}$ day, representing the participants who are tracking their medicament device use on that day. An active participant is defined as having a sensor that is on and capable of transmitting data, however not all active participants use their medicament device on any given day. The number of active participants each day is used as an offset to adjust for bias. $\varepsilon_i$ is the model error term.

Training the model includes determining the coefficients $\beta_0$ and $\beta_1$ by fitting the function of Equation 2 to historical data, for example by maximizing a likelihood function. Once the coefficients $\beta_0$ and $\beta_1$ have been trained, the estimation module 510 uses input data, Equation 2, and determined coefficients from the coefficient database 535 to determine the estimated number of medicament device use events $E(Y_i)$. In the case of predicting immediate usage events (i.e., usage events predicted to occur in the near future), the estimation module 510 generates an estimate of the number of medicament device use events per day. In the case of predicting time-lagged usage events, the data management module 136 generates time-lagged environmental predictors, for example by averaging input data entries across locations over a specified time period (e.g., 3 days).

The estimate may be made for an individual patient or user based on input data regarding that user. Alternatively, the estimate may correspond to a group of patients that share one or more characteristics determined from input data. In the case of a group of patients, the estimation module 510 may use averaged input data across group members that corresponds to the same day. For input data types that are spatially resolved, a single mean statistic averaged from all the locations of medicament device use each day is used.

V.B.2 Adjusted Zero-Truncated Negative Binomial Submodels

Another type of submodel may use an adjusted zero-truncated negative binomial logistic regression to generate event estimates that better reflect the varying impact of different types of input data on those estimates. The adjusted models include multiple environmental factors that might influence event occurrences simultaneously, for example air pollution, pollen and meteorological data. An example submodel function is given by:

$$\log(E(Y_i)) = \beta_0 + \beta_1 * X_{1i} + \beta_2 * X_{2i} + \beta_3 * X_{3i} + \log(A_i) + \varepsilon_i \quad \text{(Equation 3)}$$

where $X_{1i}$ is a vector of air pollution for the $i^{th}$ day, $X_{2i}$ is a vector of pollen and mold spore measurements for the $i^{th}$ day and $X_{3i}$ is a vector of meteorological information for the $i^{th}$ day. Due to the collinearity between air pollutants, separate models are developed for AQI and each pollutant. Similar to the unadjusted model from the prior subsection, estimates may be immediate or time-lagged.

V.B.3 Generalized Linear Mixed Submodel with Repeated Measures

Another type of submodel uses generalized linear mixed models with repeated measures to determine individual medicament device use estimates using surroundings data and individual data. For each patient using this model, individual data includes tracked start date, end date and active days the patient has recorded medicament device use. For active days on which a patient experiences a medicament device use event, the data management module 136 selects corresponding surroundings data based on the time and location of the event. If location data are not available, regional mean statistics at the time of exposure are applied. For those active days on which a patient does not experience a medicament device use event, the data management module 136 selects the corresponding regional mean exposure statistics for each day. In various embodiments, the submodels control for person-level confounding by including race-ethnicity, gender, smoking status and pet ownership.

In one embodiment, the submodel function is as follows:

$$\log \text{it}(pr[Y_{ij}=1|E_{ij},P_i,\beta])=\beta_0+\beta_1 E_{ij}+\beta_2 P_i+\gamma_i+\varepsilon_{ij} \quad \text{(Equation 4)}$$

where $Y_{ij}$ is whether patient i experiences a medicament device use event during the j-th (j=1, ..., $n_i$) time/day when the patient is active in the program and $E_{ij}$ is patient i's corresponding exposure during time/day j determined from surroundings data. $P_i$ is a vector of individual level confounding factors including race-ethnicity, gender, smoking status and pet ownership. $\gamma_i$ is the random effect of patient i and $\varepsilon_{ij}$ is the error term of patient i during time/day j. The various $\beta$ terms are the submodel coefficient vectors.

Submodel training and use is similar to the models described above. The above analysis identifies the impacts of immediate exposure on respiratory disease exacerbation at individual level. Thus, estimates can be generated based on $Y_{ij}$ regarding a patient's risk of an respiratory disease or medicament device usage event in the near future. Similar to the models described above, estimates may be immediate or time-lagged.

V.B.4 Shared Frailty Submodels with Repeated Measures

Another type of submodel uses shared frailty models with repeated measures. The shared frailty model is a special case of a Cox proportional hazard model that deals with survival data. It has recurrent events (e.g., morbidity) and may or may not have terminal events (e.g., death). This allows a submodel of this type to treat events, such as rescue inhaler uses for an individual as recurrent events, which allows for numerical representation of the lack of independence of those recurrent events for each patient. A submodel of this type assumes that subjects vary in their respiratory disease susceptibility, severity and disease management, and therefore also vary in their likelihood of experiencing events.

A submodel of this type represents these recurring events in a frailty term that can be considered a random covariate in the submodel that corrects for dependence among the multiple medicament device usage events. Input data used to train the submodel to generate coefficients or run the submodel to determine estimates may require processing and/or specific interpretation by the submodel. For example, historical or current rescue events will be one type of input to the model. The submodel may be configured to determine that one event time starts from the ending of a medicament device use and ends with the occurrence of the next event. The cumulative environmental exposure during an event time is used to predict its time-to-event (e.g., time to rescue inhaler use). Left truncation is performed when the previous ending time of a rescue event cannot be identified. Similarly, right-censoring could happen when time associated with the occurrence of the next event cannot be identified (e.g., for the rescue event before the current time).

In one embodiment, the submodel function 640 is as follows:

$$\lambda_{ij}(t|\gamma_i) = \gamma_i \lambda_0(t) \exp(\beta^T X_{ij}) = \gamma_i \lambda_{ij}(t) \quad \text{(Equation 5)}$$

where for the j-th (j=1, ..., $n_i$) observation of the i-th patient (i=1, ..., G), let $T_{ij}$ denote the recurrent event times under study, let $C_{ij}$ be the right-censoring times and let $L_{ij}$ be the left truncation times. The observations $Y_{ij}$ equal to min($T_{ij}$, $C_{ij}$) and the censoring indicators are $\delta_{ij} = I_{[Y_{ij} = T_{ij}]}$. Further, $\lambda_0(t)$ is the baseline hazard function, $X_{ij}$ is the covariate vector of event time cumulative exposure associated with the vector of regression parameters β.

Similarly to the generalized linear mixed models with repeated measures from Section V.B.3 above, in some embodiments, this type of submodel may control for individual confounding including age, gender, demographic information, smoking status, education levels and other individual data variables. $\gamma_i$ is the random effect associated with individual i. The submodels assume that the $\gamma_i$ are independently and identically distributed (i.i.d) from a gamma distribution with E($\gamma_i$)=1 and Var($\gamma_i$)=θ. To evaluate potential effect modification by gender, the estimates are modeled separately for males and females.

A patient may experience respiratory disease symptoms and use their medicament device at home and anywhere in the community during their daily lives, therefore the spatial signal of an individual's medicament device use is not limited to one geographic neighborhood. To address this spatial variability, variations on this type of shared frailty submodel may be used. For example, both single-level (e.g., the example submodel function above) may be used, as well as multi-level frailty modeling techniques (not explicitly shown). A multi-level approach may include a submodel function with a 2-level (individual and zip/census tract) or a 3-level (individual, zip/census tract and county) modeling function, with different regression coefficients for each level, to allow estimates generated by the submodel to identify neighborhood clustering effects on medicament device use.

V.C. Applying Submodels to Generate Model Outputs

As discussed above, the submodels modules 132 estimate respiratory disease risk, medicament device usage, exacerbations, and healthcare utilization and determine predictors of those risks. Outputs from one or more of the submodels may be combined by model modules 134 to convert those submodel estimates and predictors into more easily interpreted actionable information (herein referred to as "model estimates" for clarity) by patients, family members, healthcare providers, and other interested parties.

How and when model estimates are generated and converted into actionable information sent to users may vary based on the user case and implementation of server 130. For example, submodel estimates may be generated on a fixed schedule, by a request of a user, or upon the occurrence of an event such as a rescue inhaler usage event, an exacerbation, or a healthcare utilization. The client communication module 135 may receive information from a client device 110 for use in generating the estimates. Information received from the client device 110 may include the device location, usage event information, and other user information. The model modules 134 use submodel estimates and information received from the client device 110 to generate model estimates that are included in output data from the application server 130. Model estimates may be sent to a client device for display to a user. The model modules 134 may use model estimates to create visualizations or other user interface constructs such as maps, graphics, text displays, and the like for presentation to users. The model modules 134 may further use model estimates to create information, such as EHR and EMR entries, to provide to information management systems and other external systems.

V.C.1 Assessment of Regional Risk Due to Current Conditions

In one embodiment, a model module 134 generates an assessment of geographic regional risk (e.g., asthma risk, COPD risk) by identifying the key variables within the surroundings data that significantly influence medication use in a region under current or historic conditions. In one embodiment, the model module 134 identifies the predictors in assessing geographic regional risk by identifying the submodel coefficients that have high significance values with respect to rescue use predictiveness. The model estimates the impacts of different types of surroundings data, considering both immediate and lagged exposures. This model can be provided to regional decision-makers to inform interventions such as pollution control or deforestation prevention efforts.

Figure 7:
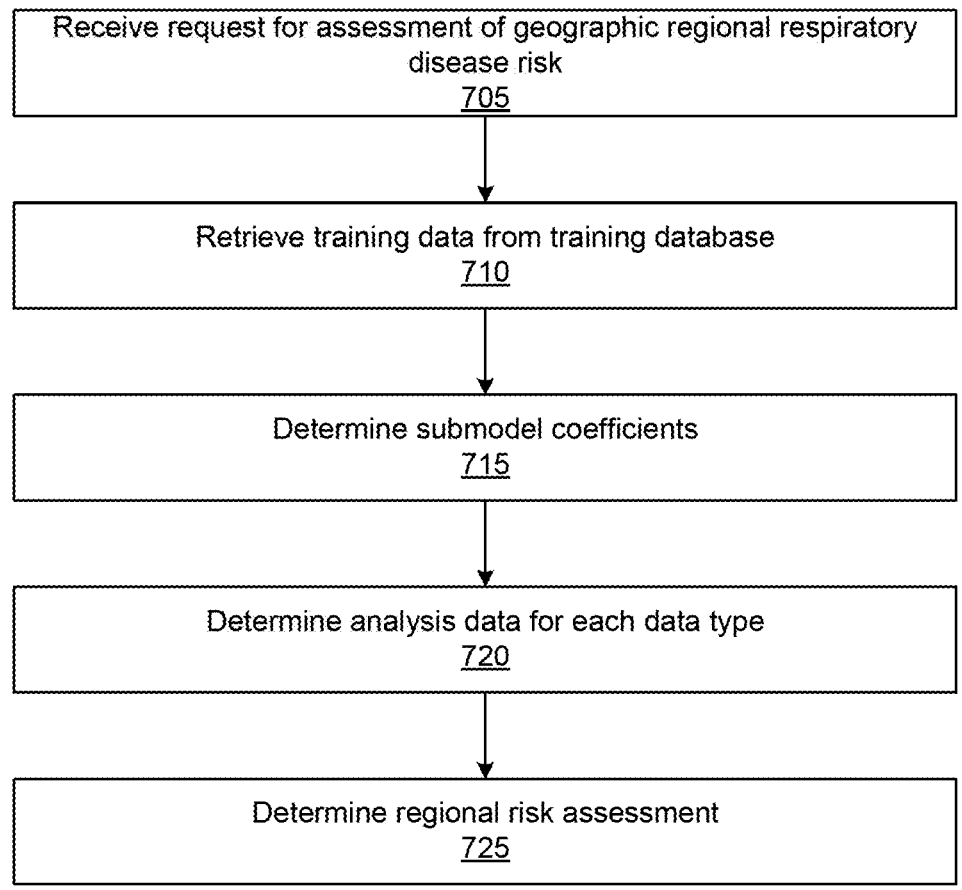
FIG. 7 shows a flowchart for implementing a model that provides an assessment of regional risk due to current conditions, according to one embodiment.

FIG. 7 shows a flowchart for implementing a model that provides an assessment of regional risk due to current conditions, according to one embodiment. The model module 134 receives 705 a request for an assessment of geographic regional risk. The request includes information about the geographic region for which the assessment is requested. The submodel module 132 retrieves 710 training data from the training database 530 that is relevant to the indicated geographic region. In one embodiment, the training data contains relative values such that the values of the coefficients may be compared to one another. In the example of FIG. 7, the submodel module 132 uses Equation 2 from Section V.B.1. The submodel module 132 determines 715 submodel coefficients based on the training data and Equation 2 as described above in Section V.B.1. In various embodiments, one or more other models from Section V.B. are used. The submodel module 132 determines 720 analysis data, such as significance and association values for each data type based on the fit of Equation 2 with the determined coefficients to a set of surroundings data. The model module 134 determines 725 a regional risk assessment based on the analysis data. In one embodiment, the regional risk assessment identifies which input data types are particularly influential on respiratory disease risk. In one embodiment, the output of the model module 134 is similar to Table 4.

V.C.2 Estimation of the Potential Impact of Regional Interventions on Respiratory Disease In one embodiment, the model module 134 generates estimates of the potential impact of regional interventions on respiratory disease. The models predict the impact of various regional interventions (e.g., air pollution mitigation or improvement, neighborhood greening, traffic calming or diversion, public transportation enhancements) on regional respiratory disease burden. Specifically, the model estimates the reduction in respiratory disease burden (defined as rescue medication use or translated into utilization and cost) as a result of specific intervention efforts.

Figure 8:
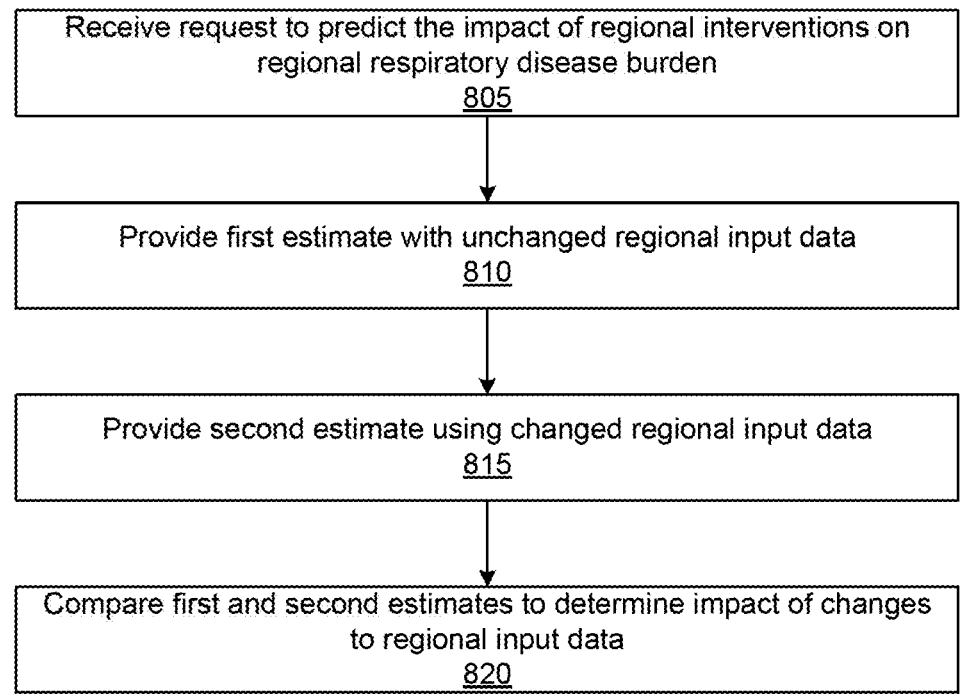
FIG. 8 shows a flowchart for implementing a model that generates estimates of the potential impact of regional interventions on respiratory disease burden, according to one embodiment.

FIG. 8 shows a flowchart for implementing a model that generates estimates of the potential impact of regional interventions on respiratory disease burden, according to one embodiment. The model module 134 receives 805 a request to predict the impact of various regional interventions on regional respiratory disease burden. In one embodiment, the database server 140 has a regional input data set containing data for the region, and the request includes one or more changes to the regional input data set for different time periods. The changes to the regional input data relate to the regional interventions and may represent improved pollution, increased green space, different weather patterns, and the like. The submodel module 132 provides 810 a first estimate, $E(Y_1)$, using Equation 2 from Section V.B.1. above with the unchanged regional input data set as input data to establish a baseline against which changes may be measured. In various embodiments, one or more other models from Section V.B. are used. The submodel 132 provides 815 a second estimate, $E(Y_2)$, using the changed regional input data set as input data. The model module 134 compares 820 $E(Y_1)$ and $E(Y_2)$ to determine the impact of the changes to the regional input data.

V.C.3 Development of a National Respiratory Disease Risk Map and Score

In one embodiment, the model module 134 generates a national respiratory disease risk map and score, where the risk of respiratory disease medication use, exacerbations, or healthcare utilization is defined geographically based upon underlying surroundings data. Geographic units, including metropolitan areas, counties, zip codes. census tracts, block groups or blocks, can be assigned a respiratory disease risk score based upon these conditions. Specifically, the model predicts the respiratory disease risk for defined geographic units, based upon the surroundings data of that area. The score assigned to each geographic unit may be used to create a map. The map can be provided to local decision-makers to identify high-risk respiratory disease areas or to real estate applications (e.g., ZILLOW, TRULIA, REDFIN) to make recommendations about where families should purchase a home or rent based upon their health conditions. The map can also be used by governments to identify the areas in which interventions to reduce the burden of respiratory disease should occur.

Figure 9:
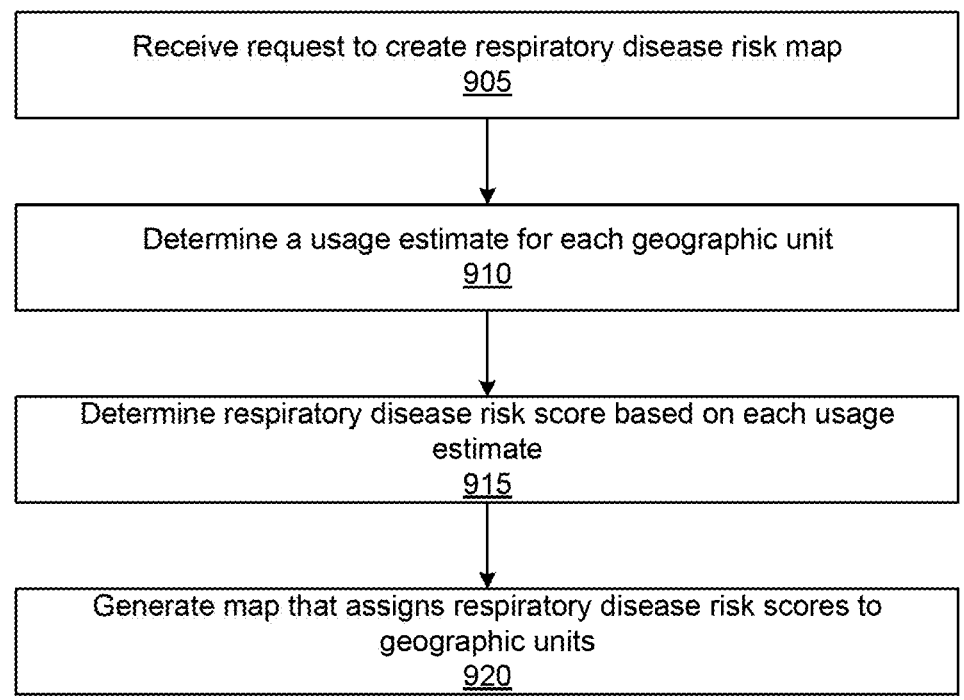
FIG. 9 shows a flowchart for generating a national respiratory disease risk map and score, according to one embodiment.

FIG. 9 shows a flowchart for generating a national respiratory disease risk map and score, according to one embodiment. The model module 134 receives 905 a request to create a respiratory disease risk map. The request includes information about the geographic units, including how many geographic units the map will have and the location and boundaries of the geographic units. For each geographic unit, the submodel module 132 determines 910 a usage estimate E(Y) using Equation 3 from section V.B.2. The model module 134 determines 915 a respiratory disease risk score based on each usage estimate. The respiratory disease risk score may be a raw output of a submodel, a function of one or more submodel outputs (e.g., a linear combination). In one embodiment, respiratory disease risk scores are assigned to groups for different ranges (e.g., high, medium, low), and may have color coding. The model module 134 generates 920 a map that assigns each respiratory disease risk score to its respective geographic unit.

V.C.4 Assessment of Future Regional Risk Due to Changing Climate or Other Shifting Environmental or Built Environment Factors In one embodiment, the model module 134 generates effect estimates for all surroundings data types, allowing the model module to predict how the respiratory disease risk will change in the future with changing conditions. The model predicts future respiratory disease risk for geographic units and may provide a map for visualization. The map can be provided to local decision-makers to identify high-risk respiratory disease areas or to real estate applications (e.g., ZILLOW, TRULIA, REDFIN) to make recommendations about where families should purchase a home or rent based upon their health conditions. The map can also be used by governments to identify the areas in which interventions to reduce the burden of respiratory disease should occur to address the impacts of shifting environmental or built environment factors.

Figure 10:
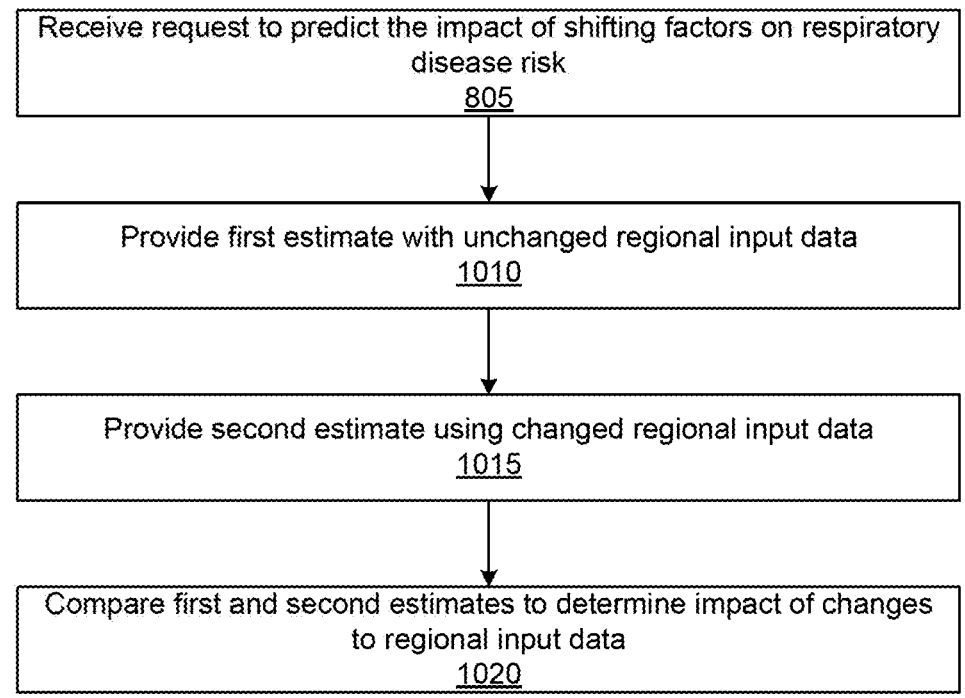
FIG. 10 shows a flowchart for implementing a model that generates estimates of the potential impact of shifting factors on respiratory disease risk, according to one embodiment.

One implementation of the model may be similar to the process of FIG. 8, but with changes to the regional input data that represent shifting factors such as climate change or environmental changes instead of intervention strategies. FIG. 10 shows a flowchart for implementing a model that generates estimates of the potential impact of shifting factors on respiratory disease risk, according to one embodiment. The model module 134 receives 1005 a request to predict the impact of shifting factors on respiratory disease risk. In one embodiment, the database server 140 has a regional input data set containing data for the region, and the request includes one or more changes to the regional input data set for different time periods. The changes to the regional input data relate to the shifting factors such as climate change and environmental changes. The submodel module 132 provides 1010 a first estimate, $E(Y_1)$, using Equation 2 from Section V.B.1. above with the unchanged region input data set as input data to establish a baseline against which changes may be measured. In various embodiments, one or more other models from Section V.B. are used. The submodel 132 provides 1015 a second estimate, $E(Y_2)$, using the changed regional input data set as input data. The model module 134 compares 1020 $E(Y_1)$ and $E(Y_2)$ to determine 1020 the impact of the changes to the regional input data.

Figure 11:
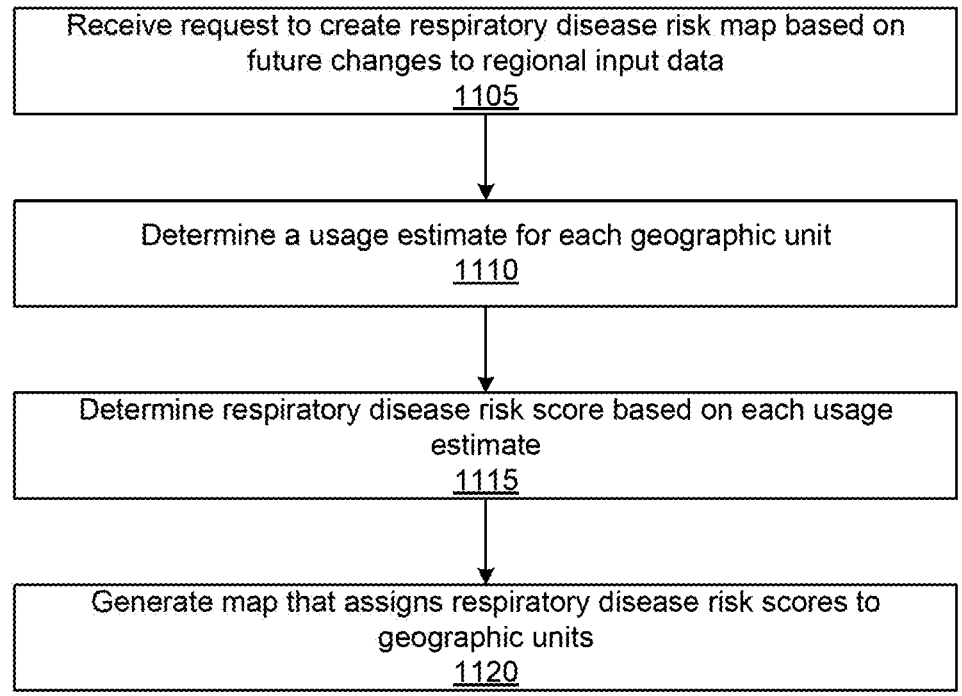
FIG. 11 shows a flowchart for generating a future national respiratory disease risk map and score, according to one embodiment.

FIG. 11 shows a flowchart for generating a future national respiratory disease risk map and score, according to one embodiment. The model module 134 receives 1105 a request to create a respiratory disease risk map based on estimated future changes to regional input data. The request includes information about the geographic units, including how many geographic units the map will have and the location and boundaries of the geographic units. The request further includes estimated changes to regional input data. For each geographic unit, the submodel module 132 determines 1110 a usage estimate E(Y) using Equation 3 from section V.B.2. In various embodiments, one or more other models from Section V.B. are used. The model module 134 determines 1115 a respiratory disease risk score based on each usage estimate. The respiratory disease risk score may be a raw output of a submodel, a function of one or more submodel outputs (e.g., a linear combination). In one embodiment, respiratory disease risk scores are assigned to groups for different ranges (e.g., high, medium, low), and may have color coding. The model module 134 generates 1120 a map that assigns each respiratory disease risk score to its respective geographic unit.

V.C.5 Gaining Insights About Person-Level Environmental Sensitivities

In one embodiment, the model module 134 generates person-level information about environmental sensitivities. The model generates personalized insights generated about environmental conditions in which a user has used their rescue medications or experienced exacerbations or healthcare utilization. In various embodiments, these insights are presented as a notification or graphical representation in a mobile app and web dashboard. The insights may be paired with actionable information, based on national guidelines, about how the user can address these sensitivities through behavior change, trigger avoidance, mitigation or other activities.

Figure 12:
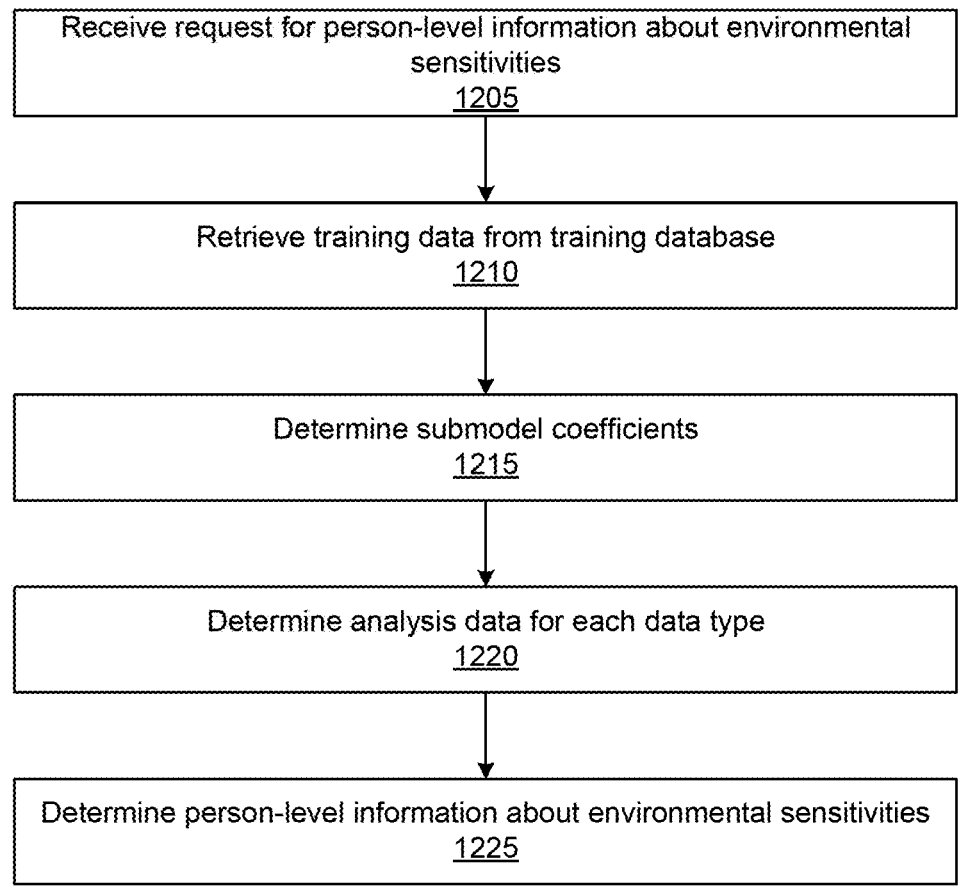
FIG. 12 shows a flowchart for generating person-level information about environmental sensitivities, according to one embodiment.

FIG. 12 shows a flowchart for generating person-level information about environmental sensitivities, according to one embodiment. The model module 134 receives 1205 a request for person-level information about environmental sensitivities. The request includes information about the individual for which the assessment is requested. The submodel module 132 retrieves 1210 training data from the training database 530 that is relevant to the indicated individual. In the example of FIG. 12, the submodel module 132 uses Equation 2 from Section V.B.1. The submodel module 132 determines 1215 submodel coefficients based on the training data and Equation 2 as described above in Section V.B.1. In various embodiments, one or more other models from Section V.B. are used. The submodel module 132 determines 1220 analysis data, such as significance and association values for each data type based on the fit of Equation 2 with the determined coefficients to a set of surroundings data. The model module 134 determines 1225 person-level information about environmental sensitivities based on the analysis data. In one embodiment, the person-level information about environmental sensitivities identifies which input data types are particularly influential on respiratory disease risk for the individual.

V.C.6 Predicting Person-Level Future Rescue Medication Use, Exacerbation, or Healthcare Utilization Based on Environmental Conditions In one embodiment, the model module 134 generates specific estimates about when an individual might use their rescue medication, experience exacerbation, or have a healthcare utilization event in the future due to a combination of individual data and surroundings data. Example individual data used by this model includes adherence in the past week or month, current respiratory disease control, and individual characteristics. Example surroundings data includes predicted weather and air pollution levels in the following 1-7 days. These estimates may be presented as a notification or graphical representation in the mobile app and web dashboard. The estimates may be paired with actionable information, based on national guidelines about how the user can address this potential medication use through improved adherence, behavior change, trigger avoidance, mitigation or other activities. The model can also be provided to local healthcare system partners so that they can predict when respiratory disease-related utilization may occur and plan for staffing or space needs in their health facilities.

Figure 13:
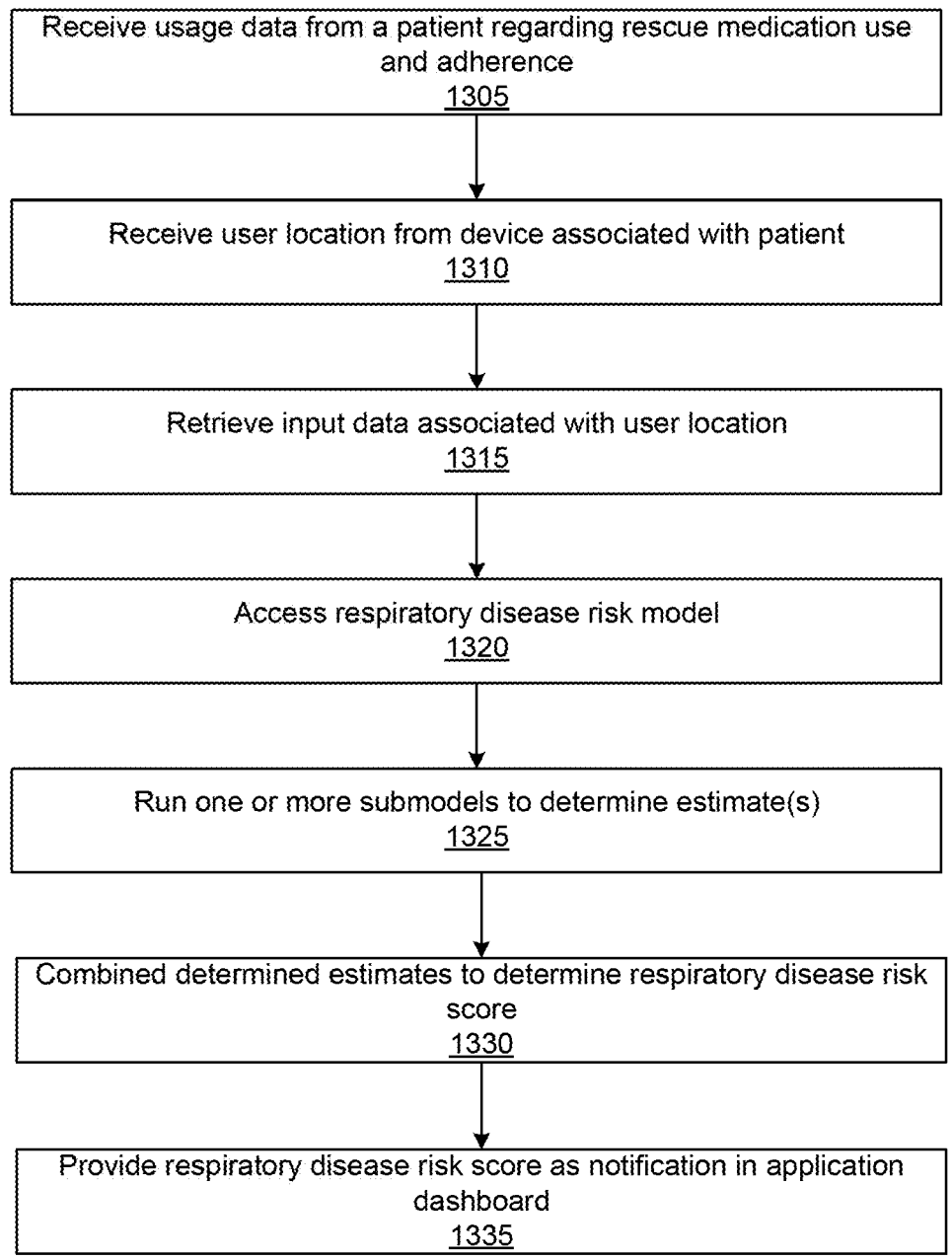
FIG. 13 shows a flowchart for generating estimates about individual rescue medication use, according to one embodiment.

FIG. 13 shows a flowchart for generating estimates about individual rescue medication use, exacerbation, or healthcare utilization, according to one embodiment. The application server 130 receives 1305 usage data from a patient regarding rescue medication use and adherence over a period of time. The model module 134 receives 1310 a user location from a device associated with the patient for use in determining regional characteristics for the model. The model module 134 retrieves 1315 input data related to the user location from the database server 140. The model module 134 accesses 1320 a respiratory disease risk model for estimating individual rescue medication use. The respiratory disease risk model may use one or more of the submodels described in Section V.B. above. The submodel module 132 determines 1325 an estimate E(Y) for each submodel. The model module 134 combines 1330 the determined estimates to determine a respiratory disease risk. The respiratory disease risk score may be a raw output of a submodel, a function of one or more submodel outputs (e.g., a linear combination). In one embodiment, respiratory disease risk scores are assigned to groups for different ranges (e.g., high, medium, low), and may have color coding. The model module 134 generates 920 a map that assigns each respiratory disease risk score to its respective geographic unit. The application server 130 provides 1335 the respiratory disease risk score as a notification in an application dashboard to notify a user about the respiratory disease risk.

In one embodiment, instead of a rescue medication use, the model module 134 generates specific estimates about when an individual might experience a healthcare utilization (defined as a prescription of systemic corticosteroids, an emergency department visit or an inpatient visit) in the future due to a combination of information such as adherence in the past week or month, current respiratory disease control, individual characteristics, and predicted weather and air pollution levels in the following 1-7 days. These estimates would be presented as a notification or graphical representation in the mobile app and web dashboard. The estimates would be paired with actionable information, based on national guidelines, about how the user can address this potential medication use through improved adherence, behavior change, trigger avoidance, mitigation or other activities.

VI. Additional Considerations

It is to be understood that the figures and descriptions of the present disclosure have been simplified to illustrate elements that are relevant for a clear understanding of the present disclosure, while eliminating, for the purpose of clarity, many other elements found in a typical system. Those of ordinary skill in the art may recognize that other elements and/or steps are desirable and/or required in implementing the present disclosure. However, because such elements and steps are well known in the art, and because they do not facilitate a better understanding of the present disclosure, a discussion of such elements and steps is not provided herein. The disclosure herein is directed to all such variations and modifications to such elements and methods known to those skilled in the art.

Some portions of above description describe the embodiments in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the invention. This description should be read to include one or at least one and the singular also includes the plural unless it is obvious that it is meant otherwise.

While particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope of this description.

The invention claimed is:

1. A method comprising:
   accessing a respiratory disease risk model trained using training data received for a geographic region, the respiratory disease risk model comprising a negative binomial submodel trained to predict an expected incidence of medication usage events for a user in the geographic region at a receipt time and a land use regression submodel trained to predict air quality data and meteorological data for the geographic region at the receipt time, wherein the respiratory disease risk model determines the expected respiratory disease risk for the user based on the expected incidence of medication usage events for the user, air quality data, and meteorological data for the geographic region at the receipt time;
   identifying a user at a current receipt time and a location of the user in a geographic region;
   predicting, for the current receipt time, air quality data, and meteorological data recorded for the geographic region of the identified user;
   inputting, to the trained respiratory disease risk model, the predicted air quality data and the meteorological data for the current receipt time to generate an expected incidence of medication usage events for the identified user at the current receipt time;
   determining a recommended action based on the expected incidence of medication usage events for the identified user; and
   sending a respiratory disease risk notification to a computing device associated with the identified user in the geographic region including the recommended action and the expected incidence of medication usage events.

2. The method of claim 1, wherein air quality data predicted by the land use regression submodel includes at least one of hourly air quality information and daily air quality information.

3. The method of claim 1, wherein meteorological data predicted by the land use regression submodel includes weather information within an hour of the receipt time.

4. The method of claim 1, wherein the respiratory disease risk model comprises an immediate environment trigger submodel correlating air quality data and meteorological data close in proximity in time to the expected incidence of medication usage events as a function of user location, wherein the environment trigger submodel is an adjusted linear regression model.

5. The method of claim 1, wherein the respiratory disease risk model further comprises a linear mixed submodel correlating local air quality data and meteorological data close in proximity in time to the expected incidence of medication usage events as a function of user location.

6. The method of claim 1, wherein the respiratory disease risk model further comprises an environment factor submodel correlating environment data and land use data to the expected incidence of medication usage events as a function of user location.

7. The method of claim 1, wherein the respiratory disease risk model further comprises a shared frailty submodel correlating user data for the identified user, air quality data and meteorological data for the geographic region of the identified user with the expected incidence of medication usage of the identified user as a function of user location and previous incidences of medication usage.

8. The method of claim 1, wherein the expected respiratory disease risk comprises a risk that the identified user will experience a respiratory disease exacerbation within a threshold period of time.

9. A system for exchanging data between a sender and a recipient comprising:
   a processor for executing computer program instructions;
   a non-transitory computer-readable storage medium storing computer program instructions executable by the processor to perform steps comprising:
   access a respiratory disease risk model using training data received for a geographic region, the respiratory disease risk model comprising a negative binomial submodel trained to predict an expected incidence of medication usage events for a user in the geographic region at a receipt time and a land use regression submodel trained to predict air quality data and meteorological data for the geographic region at the receipt time, wherein the respiratory disease risk model determines the expected respiratory disease risk for the user based on the expected incidence of medication usage events for the user, air quality data, and meteorological data for the geographic region at the receipt time;
   identify a user at a current receipt time and a location of the user in a geographic region;
   predicting, for the current receipt time, air quality data, and meteorological data recorded for the geographic region of the identified user;
   input, to the trained respiratory disease risk model, the predicted air quality data and the meteorological data for the current receipt time to generate an expected incidence of medication usage events for the identified user at the current receipt time;
   determine a recommended action based on the expected incidence of medication usage events for the identified user; and
   send a respiratory disease risk notification to a computing device associated with the identified user in the geographic region including the recommended action and the expected incidence of medication usage events.

10. The system of claim 9, wherein air quality data predicted by the land use regression submodel includes at least one of hourly air quality information and daily air quality information.

11. The system of claim 9, wherein the respiratory disease risk model comprises an immediate environment trigger submodel correlating air quality data and meteorological data close in proximity in time to the expected incidence of medication usage events as a function of user location, wherein the environment trigger submodel is an adjusted linear regression model.

12. The system of claim 9, wherein the respiratory disease risk model further comprises a linear mixed submodel correlating local air quality data and meteorological data close in proximity in time to the expected incidence of medication usage events as a function of user location.

13. The system of claim 9, wherein the respiratory disease risk model further comprises an environment factor submodel correlating environment data and land use data to the expected incidence of medication usage events as a function of user location.

14. A non-transitory computer-readable storage medium storing computer program instructions executable by a processor to perform steps comprising:
   accessing a respiratory disease risk model trained using training data received for a geographic region, the respiratory disease risk model comprising a negative binomial submodel trained to predict an expected incidence of medication usage events for a user in the geographic region at a receipt time and a land use regression submodel trained to predict air quality data and meteorological data for the geographic region at the receipt time, wherein the respiratory disease risk model determines the expected respiratory disease risk for the user based on the expected incidence of medication usage events for the user, air quality data, and meteorological data for the geographic region at the receipt time;
   identifying a user at a current receipt time and a location of the user in a geographic region;
   predicting, for the current receipt time, air quality data, and meteorological data recorded for the geographic region of the identified user;
   inputting, to the trained respiratory disease risk model, the predicted air quality data and the meteorological data for the current receipt time to generate an expected incidence of medication usage events for the identified user at the current receipt time;
   determining a recommended action based on the expected incidence of medication usage events for the identified user; and
   sending a respiratory disease risk notification to a computing device associated with the identified user in the geographic region including the recommended action and the expected incidence of medication usage events.

15. The non-transitory computer-readable storage medium of claim 14, wherein air quality data predicted by the land use regression submodel includes at least one of hourly air quality information and daily air quality information.

16. The non-transitory computer-readable storage medium of claim 14, wherein the respiratory disease risk model further comprises a shared frailty submodel correlating user data for the identified user, air quality data and meteorological data for the geographic region of the identified user with the expected incidence of medication usage of the identified user as a function of user location and previous incidences of medication usage.

17. The non-transitory computer-readable storage medium of claim 14, wherein the expected respiratory disease risk comprises a risk that the identified user will experience a respiratory disease exacerbation within a threshold period of time.

18. A method comprising:
   accessing a respiratory disease risk model trained to determine a future expected disease risk for a user by correlating future air quality data, future meteorological data, and future environment and land use data for a geographic region with an expected incidence of medication usage events for the user, the respiratory disease risk model comprising:
      a negative binomial submodel trained to predict an expected incidence of medication usage events for a user in the geographic region at a receipt time;
      a time-lagged trigger submodel trained to predict air quality data and meteorological data for the geographic region close in proximity in time to expected incidence of medication usage events, wherein the meteorological data includes weather information; and
      an environment factor submodel trained to predict environment and land use data for the geographic region, wherein environment and land use data classifying land use and land vegetation cover;
   identifying a user at a current receipt time and a location of the user in a geographic region;
   predicting, for the current receipt time, air quality data, meteorological data, and environment and land use data for the geographic region of the identified user;
   inputting, to the trained respiratory disease risk model, the geographic region, the air quality data, the local meteorological data, and the environment and land use data predicted for the geographic region generate an expected respiratory disease risk for the geographic region of the identified user;
   determining a recommended action for the identified user based on the expected respiratory disease risk; and
   sending a respiratory disease risk notification to a computing device associated with the identified user for presentation to the identified user including the recommended action and the expected future respiratory disease risk.

19. A method comprising:
   accessing a respiratory disease risk model trained to determine a future expected disease risk for a user by correlating future air quality data, future meteorological data, and future environment and land use data for a geographic region with an expected incidence of medication usage events for the user, the respiratory disease risk model comprising:
      a negative binomial submodel trained to predict an expected incidence of medication usage events for a user in the geographic region at a receipt time;
      a time-lagged trigger submodel trained to predict future air quality data and future meteorological data for the geographic region close in proximity in time to expected incidence of medication usage events, wherein the future meteorological data includes weather information; and
      an environment factor submodel trained to predict future environment and land use data for the geographic region, wherein future environment and land use data classifying land use and land vegetation cover;
   identifying a user at a current receipt time and a location of the user in a geographic region;
   predicting, for the current receipt time, future air quality data, future meteorological data, and future environment and land use data for the geographic region of the identified user;

inputting, to the trained respiratory disease risk model, the geographic region, the future air quality data, the future local meteorological data, and the future environment and land use data predicted for the geographic region generate an expected future respiratory disease risk for the geographic region of the identified user;

determining a recommended action for the identified user based on the expected future respiratory disease risk; and sending a respiratory disease risk notification to a computing device associated with the identified user for presentation to the identified user including the recommended action and the expected future respiratory disease risk.

20. A method comprising:

accessing a respiratory disease risk model trained to determine a future expected disease risk for a user by correlating future air quality data, future meteorological data, and future environment and land use data for a geographic region with an expected incidence of medication usage events for the user, the respiratory disease risk model comprising:

a negative binomial submodel trained to predict an expected incidence of medication usage events for a user in the geographic region at a receipt time;

a time-lagged trigger submodel correlating air quality data and meteorological data for the geographic region close in proximity in time to expected incidence of medication usage events, wherein the meteorological data includes weather information; and an environment factor submodel trained to predict environment and land use data for the geographic region, wherein environment and land use data classifying land use and land vegetation cover;

receiving a real estate property location from a computing device at a current receipt time;

predicting, for the real estate property location, air quality data, meteorological data, and environment and land use data at the current receipt time;

inputting, to the trained respiratory disease risk model, the property location, the air quality data, the meteorological data, and the environment and land use data predicted for the real estate property location to generate an expected respiratory disease risk for the property location; and providing the expected respiratory disease risk to the computing device in response to the receipt of the property location.

* * * * *